United States Patent [19]
Elledge et al.

[11] Patent Number: 5,851,808
[45] Date of Patent: Dec. 22, 1998

[54] RAPID SUBCLONING USING SITE-SPECIFIC RECOMBINATION

[75] Inventors: Stephen J. Elledge; Qinghua Liu, both of Houston, Tex.

[73] Assignee: Baylor College of Medicine

[21] Appl. No.: 864,224

[22] Filed: Feb. 28, 1997

[51] Int. Cl.$^6$ .............................. C12N 5/09; C12N 15/63; C12N 15/64; C12N 15/66
[52] U.S. Cl. ................................ 435/172.3; 435/320.1; 536/23.1
[58] Field of Search .............................. 435/320.1, 172.3; 536/23.1

[56] References Cited

U.S. PATENT DOCUMENTS 5,102,797  4/1992  Tucker et al. ......................... 435/172.3

OTHER PUBLICATIONS

Hasan et al., Gene 150:51–56 (1994)].
Holt et al., Gene 133:95–97 (1993).
Elledge et al., Proc. Natl. Acad. Sci. USA 88:1731–1735 (1991).
Brunelli et al., BioTechniques 16(6):1061–1064 (1994).
Stryer, *Biochemistry*, 2nd ed., W.H. Freeman and Co., San Francisco, CA (1981), p. 610.
Sambrook, J. et al., *Molecular Cloning: A Laboratory Manual*, 2nd ed., Cold Spring Harbor Laboratory Press, New York (1989) pp. 16.6–16.8.
Maniatis et al., "Regulation of Inducible and Tissue–Specific Gene Expression," *Science* 236:1237–1245 (1987).
Voss et al., "The role of enhancers in the regulation of cell–type–specific transcriptional control," *Trends Biochem. Sci.*, 11:287–289 (1986).
Dijkema et al., "Cloning and expression of the chromosomal immune interferon gene of the rate," *EMBO J.* 4:761–767 (1985).
Uetsuki et al., "Isolation and Characterization of the Human Chromosomal Gene for Polypeptide Chain Elongation Factor–1α*," *J. Biol. Chem.*, 264:5791–5798 (1989).

Kim et al., "Use of the human elongation factor 1α promoter as a versatile and efficient expression system," *Gene* 92:217–223 (1990).
Mizushima and Nagata, "pEF–BOS, a powerful mammalian expression vector," *Nuc. Acids. Res.*, 18:5322 (1990).
Gorman et al., "The Rous sarcoma virus long terminal repeat is a strong promoter when introduced into a variety of eukaryotic cells by DNA–mediated transfection," *Proc. Natl. Acad. Sci. USA* 79:6777–6781 (1982).
Boshart et al., "A Very Strong Enhancer Is Located Upstream of an Immediate Early Gene of Human Cytomegalovirus," *Cell* 41:521–530 (1985).
Metcalf et al. (1996) "Conditionally Replicative and Conjugative Plasmids Carrying lacZα for Cloning, Mutagenesis, and Allele Replacement in Bacteria," *Plasmid* 35:1–13.
Ayres et al. (1993) "Precise Deletions in Large Bacterial Genomes by Vector–mediated Excision (VEX): The trfA Gene of Promiscuous Plasmid RK2 is Essential for Replication in Several Gram–negative Hosts," *J. Mol. Biol.* 230:174–185.
Pal et al. (1986) "P1 Plasmid Replication Role of Initiator Titration in Copy Number Control," *J. Mol. Biol.* 192:275–285.
Sugiura et al. (1992) "Minimal Essential Origin of Plasmid pSC101 Replication: Requirement of a Region Downstream of Iterons," *J. Bacteriol.* 175:5993–6001.

(List continued on next page.)

*Primary Examiner*—Johnny F. Railey, II
*Attorney, Agent, or Firm*—Medlen & Carroll, LLP

[57] ABSTRACT

The present invention provides compositions, including vectors, and methods for the rapid subcloning of nucleic acid sequences in vivo and in vitro. In particular, the invention provides vectors used to contain a gene of interest that comprise a sequence-specific recombinase target site. These vectors are used to rapidly transfer the gene of interest into any expression vector that contains a sequence-specific recombinase target site located downstream of a promoter element so that the gene of interest may be expressed.

24 Claims, 11 Drawing Sheets

OTHER PUBLICATIONS

Stenzel et al., "The Integration Host Factor of *Escherichia coli* Binds to Bent DNA at the Origin of Replication of the Plasmid pSC101," (1987) Cell 49:709.

Grindley and Kelley (1976) "Effects of Different Alleles of the *E. coli* K12 polA Gene on the Replication of Non–transferring Plasmids," *Mol. Gen. Genet.* 143:311–318.

Mendiola and de la Cruz (1989) "Specificity of Insertion of IS91, an Insertion Sequence Present in alpha–haemolysin plasmids of *Escherichia coli*," Mol. Microbiol. 3:979.

Francia and Lobo (1996) "Gene Integration in the *Escherichia coli* Chromosome Mediated by Tn21 Integrase (Int21)," *J. Bact.* 178:894–898.

Sternberg et al. (1981) "Site–specific Recombination and Its Role in the Life Cycle of Bacteriophage P1," *Cold Spring Harbor Symp. Quant. Biol.* 45:297–309.

Hoess et al. (1982) "P1 site–specific recombination: Nucleotide sequence of the recombining sites," *Proc. Natl. Acad. Sci. USA* 79:3398–3402.

Hoess et al. (1984) "Interaction of the bacteriophage P1 recombinase Cre with the recombining site loxP," *Proc. Natl. Acad. Sci. USA* 81:1026–1029.

Abremski et al. (1983) "Studies on the Properties of P1 Site–Specific Recombination: Evidence for Topologically Unlinked Products following Recombination," *Cell* 32:1301–1311.

Abremski et al. (1984) "Bacteriphage P1 Site–specific Recombination," *Journal of Biological Chemistry* 259:1509–1514.

Hoess and Abremski (1985) "Mechanism of Strand Cleavage and Exchange in the Cre–lox Site–specific Recombination System," *J. Mol. Biol.* 181:351–362.

Cox (1983) "The FLP protein of the yeast 2–$\mu$m plasmid: Expression of a eukaryotic genetic recombination system in *Escherichia coli*," *Proc. Natl. Acad. Sci. USA* 80:4223–4227.

Meyer–Lean et al. (1987) "Purification of the FLP site–specific recombinase by affinity chromatography and re–examination of basic properties of the system," *Nucleic Acids Res.* 15:6469–6488.

Babineau et al. (1985) "The FLP Protein of the 2–micron Plasmid of Yeast," *J. Biol. Chem.* 260:12313–12319.

Gronostajski and Sadowski (1985) "The FLP Protein of the 2–micron Plasmid of Yeast," *J. Biol. Chem.* 260:12328–12335.

Weisberg et al., "Site–specific recombination in Phage Lambda," In: *Lambda II*, Hendrix et al. Eds., Cold Spring Harbor Press, Cold Spring Harbor, NY (1983) pp. 211–250.

Leslie and Sherratt (1995) "Site–specific recombination in the replication terminus region of *Escherichi coli*: functional replacement of dif," *EMBO J.* 14:1561.

Lu and Churchward (1994) "Conjugative transposition: Tn916 integrase contains two independent DNA binding domains that recognize different DNA sequences," *EMBO J.* 13:1541–1548.

Mercier et al. (1990) "Structural and Functional Characterization of tnpI, a Recombinase Locus in Tn21 and Related β–Lactamase Transposons," *J. Bacteriol.* 172:3745–3757.

Flanagan et al. (1989) "Analysis of Inhibitors of the Site–specific Recombination Reaction Mediated by Tn3 Resolvase," *J. Mol. Biol.* 206:295.

Stark et al. (1989) "Site–Specific Recombination by Tn3 Resolvase: Topological Changes in the Forward and Reverse Reactions," *Cell* 58:779–790.

Sato et al. (1990) "The cisA Cistron of *Bacillus subtilis* Sporulation Gene spoIVC Encodes a Protein Homologous to a Site–Specific Recombinase," *J. Bacteriol.* 172:1092–1098.

Glasgow et al. (1989) "DNA–binding Properties of the Hin Recombinase," *J. Biol. Chem.* 264:10072–10082.

Hafter et al. (1988) "Enhancer–independent mutants of the Cin recombinase have a relaxed topological specificity," *EMBO J.* 7:3991–3996.

Malynn et al. Cell (1988) "The scid Defect Affects the Final Step of the Immunoglobin VDJ Recombinase Mechanism," 54:453–460.

Schild et al. (1990) "Cloning of three human multifunctional de novo purine biosynthetic genes by functional complementation of yeast mutations," *Proc. Natl. Acad. Sci. USA* 87:2916–2920.

Bai et al. (1996) "SKP1 Connects Cell Cycle Regulators to the Ubiquitin Proteolysis Machinery through a Novel Motif, the F–Box," *Cell* 86:263–274.

Hoess et al. (1986) "The role of the loxP spacer region in P1 site–specific recombination," *Nucleic Acids Res.* 14:2287–2300.

Gay et al. (1985) "Positive Selection Procedure for Entrapment of Insertion Sequence Elements in Gram–Negative Bacteria," *J. Bacteriol.* 164:918–1237.

Gay et al. (1983) "Cloning Structural Gene sacB, Which Codes for Exoenzyme Levansucrase of *Bacillus subtilis*: Expression of the Gene in *Escherichia coli*," *J. Bacteriol.* 153:1424–1431.

Cigan et al. (1988) "Mutational Analysis of the HIS4 Translational Initiator Region in *Saccharomyces cerevisiae*," *Mol. Cell. Biol.* 8:2964–2975.

Yoon et al. (1992) "SSL1, a Suppressor of a HIS4 5'–UTR Stem–Loop Mutation, is Essential for Translation Initiation and Affects UV Resistance in Yeast," Genes and Dev. 6:2463.

Kaniga et al., "A wide–host–range suicide vector for improving reverse genetics in Gram–negative bacteria: inactivation of the blaA gene of *Yersinia enterocolitica*," *Gene* 109(1):137–141 (1991).

Wang et al., "pDUAL: a transposon–based cosmid cloning vector for generating nested deletions and DNA sequencing templates in vivo," *Proc. Natl. Acad. Sci. USA* 90(16):7874–7878 (1993).

Palazzolo et al., "Phage lambda cDNA cloning vectors for substractive hybridization, fusion–protein synthesis and Cre–loxP automatic plasmid subcloning," *Gene* 88:25–36 (1990).

Waterhouse et al., "Combinatorial infection and in vivo recombination: a strategy for making large phage antibody repertoires," *Nucleic Acids Research* 21(9):2265–2266 (1993).

Sauer, "Functional Expression of the cre–lox Site–Specific Recombinant System in the Yeast *Saccharomyces cerevisiae*," *Molecular and Cellular Biology* 7(6):2087–2096 (1987).

Sternberg et al., "Bacteriophage P1 cre Gene and its Regulatory Region Evidence for Multiple Promoters and for Regulation by DNA Methylation," *Mol. Biol.* 187:197–212 (1986).

Tsurushita et al., "Phage display vectors for in vivo recombination of immunoglobulin heavy and light chain genes to make large combinatorial libraries," *Gene* 172:59–63 (1996).

Hoess et al., "Formation of small circular DNA molecules via an in vitro site–specific recombination system," *Gene* 40:325–329 (1985).

Kolb and Siddell, "Genomic targeting with an MBP–Cre fusion protein," *Gene* 183:53–60 (1996).

```
 (401) NotI    KpnI                        LOX
GC GGC CGC  GGT ACC  ATA ACT TCG TAT AGC ATA CAT TAT ACG AAG TTA TCT

EcoRI      SmaI    XhoI      NdeI    NcoI     BamHI    NotI
GGA ATT  CCC CGG  GCT CGA  GAA CAT  ATG GCC  ATG GGG  ATC CGC  GGC CGC

HpaI         SalI       SacI
AAT TGT TAA  CAG ATC  CGT CGA  CGA GCT  CGC TA (530)
```

CONSTRUCTION OF pGst-lox:

A

LINKER: C ATG GCT ATA ACT TCG TAT AGC ATA CAT TAT ACG AAG TTA TG (SEQ ID NO: 3)
        CGA TAT TGA AGC ATA TCG TAT GTA ATA TGC TTC AAT AC CTAG (SEQ ID NO: 4)
         NcoI                                                                     BamHI

B
                            XhoI              EcoRI
MCS: CAT ATG CCC ATG GCT CGA GGA TCC GAA TTC
     NdeI  NcoI          BamHI pGEX-2TKcs (5.0kb), Ptac, Gst, Ap^R CONSTRUCTION OF pVL1392-lox:

A

LINKER: GG CCG GAC GTC ATA ACT TCG TAT AGC ATA CAT TAT ACG AAG TTA TG (SEQ ID NO: 6)
C CTG CAG TAT TGA AGC ATA TCG TAT GTA ATA TGC TTC AAT AC CTAG (SEQ ID NO: 7)

CONSTRUCTION OF pGAL14-lox:

A

LINKER: T CGA GAC GTC ATA ACT TCG TAT AGC ATA CAT TAT ACG AAG TTA TGC (SEQ ID NO: 8)
         CTG CAG TAT TGA AGC ATA TCG TAT GTA ATA TGC TTC AAT ACG CCGG (SEQ ID NO: 9)

XhoI                                                              NotI

B

MCS: SalI/ClaI/PstI/SmaI/XmaI/SpeI/NotI/EagI/SacII/SacI

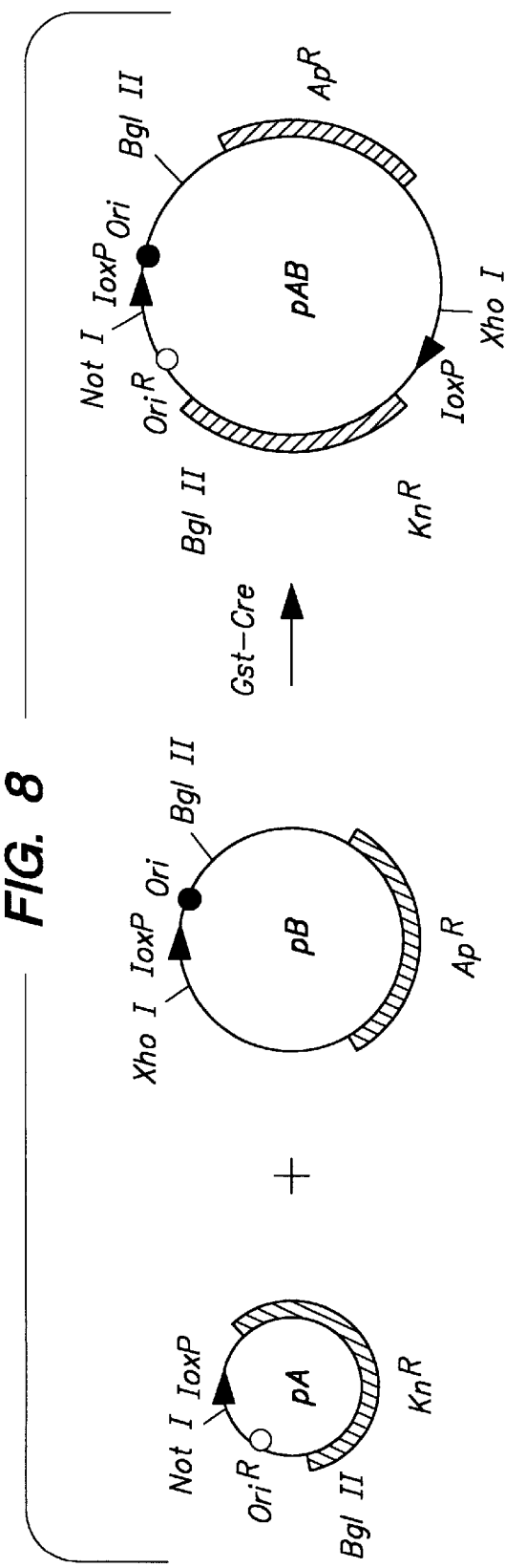
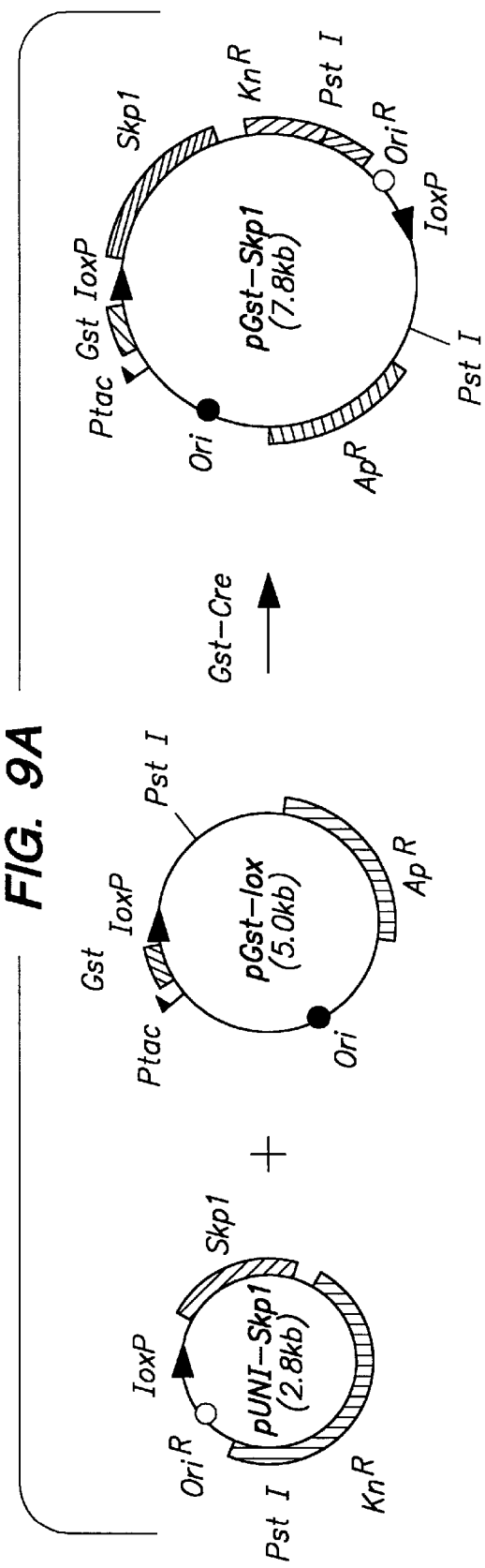
FIG. 8
FIG. 9A

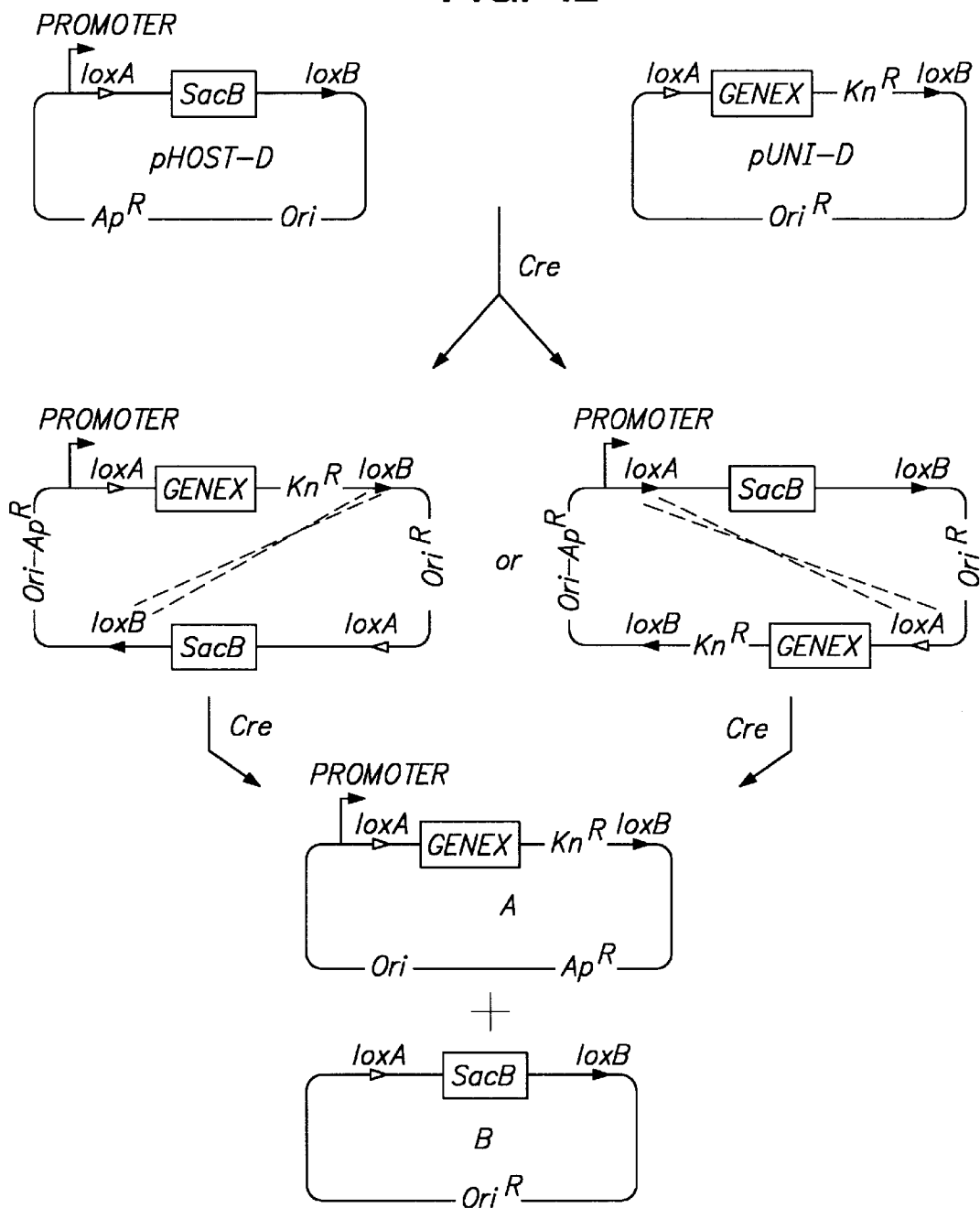

FIG. 13

```
loxP:    A T A A C T T C G T A T A      G C A T A C A T      T A T A C G A A G T T A T  (SEQ ID NO: 12)
         1 2 3 4 5 6 7 8 9 10 11 12 13                       13 12 11 10 9 8 7 6 5 4 3 2 1

T        C
                   —        —
loxP2:   A T A A C T T C G T A T A      G C A T A C A T      T A T A C G A A G T T A T  (SEQ ID NO: 13)
         1 2 3 4 5 6 7 8 9 10 11 12 13                       13 12 11 10 9 8 7 6 5 4 3 2 1

T
                                                                        —
loxP3:   A T A A C T T C G T A T A      G C A T A C A T      T A T A C G A A G T T A T  (SEQ ID NO: 14)
         1 2 3 4 5 6 7 8 9 10 11 12 13                       13 12 11 10 9 8 7 6 5 4 3 2 1

T        C                                           T
                   —        —                                           —
loxP23:  A T A A C T T C G T A T A      G C A T A C A T      T A T A C G A A G T T A T  (SEQ ID NO: 15)
         1 2 3 4 5 6 7 8 9 10 11 12 13                       13 12 11 10 9 8 7 6 5 4 3 2 1
```

RAPID SUBCLONING USING SITE-SPECIFIC RECOMBINATION

FIELD OF THE INVENTION

The invention relates to recombinant DNA technology. In particular, the invention relates to compositions, including vectors, and methods for the rapid subcloning of nucleic acid sequences in vivo and in vitro.

BACKGROUND OF THE INVENTION

Molecular biotechnology has revolutionized the production of protein and polypeptide compounds of pharmacological importance. The advent of recombinant DNA technology permitted for the first time the production of proteins on a large scale in a recombinant host cell rather than by the laborious and expensive isolation of the protein from tissues which may contain minute quantities of the desired protein (e.g., isolation of human growth hormone from cadaver pituitary). The production of proteins, including human proteins, on a large scale in a heterologous host requires the ability to express the protein of interest in the heterologous host. This process typically involves isolation or cloning of the gene encoding the protein of interest followed by transfer of the coding region into an expression vector which contains elements (e.g., promoters) which direct the expression of the desired protein in the heterologous host cell. The most commonly used means of transferring or subcloning a coding region into an expression vector involves the in vitro use of restriction endonucleases and DNA ligases. Restriction endonucleases are enzymes which generally recognize and cleave a specific DNA sequence in a double-stranded DNA molecule. Restriction enzymes are used to excise the coding region from the cloning vector and the excised DNA fragment is then joined using DNA ligase to a suitably cleaved expression vector in such a manner that a functional protein may be expressed.

The ability to transfer the desired coding region to an expression vector is often limited by the availability or suitability of restriction enzyme recognition sites. Often multiple restriction enzymes must be employed for the removal of the desired coding region and the reaction conditions used for each enzyme may differ such that it is necessary to perform the excision reactions in separate steps. In addition, it may be necessary to remove a particular enzyme used in an initial restriction enzyme reaction prior to completing all restriction enzyme digestions; this requires a time-consuming purification of the subcloning intermediate. Ideal methods for the subcloning of DNA molecules would permit the rapid transfer of the target DNA molecule from one vector to another in vitro or in vivo without the need to rely upon restriction enzyme digestions.

SUMMARY OF THE INVENTION

The present invention provides reagents and methods which comprise a system for the rapid subcloning of nucleic acid sequences in vivo and in vitro without the need to use restriction enzymes. Accordingly, the present invention provides a nucleic acid construct comprising, in operable order: a) a conditional origin of replication; b) a sequence-specific recombinase target site having a 5' and a 3' end; and c) a unique restriction enzyme site, the restriction enzyme site located adjacent to the 3' end of the sequence-specific recombinase target site. The present invention is not limited by the nature of the conditional origin of replication employed. A variety of conditional origins of replication, including temperature-sensitive replicons are known to the art and may be employed on the nucleic acid constructs of the present invention. In a preferred embodiment, the nucleic acid construct further comprises a prokaryotic termination sequence. The present invention is not limited by the nature of the prokaryotic termination sequence chosen. In one embodiment, the prokaryotic termination sequence is the T7 termination sequence. A variety of termination sequences are known to the art and may be employed in the nucleic acid constructs of the present invention including, the $T_{INT}$, $T_{L1}$, $T_{L2}$, $T_{L3}$, $TR_1$, $TR_2$, $T_{6S}$ termination signals derived from the bacteriophage lambda [Lambda II, Hendrix et al. Eds., Cold Spring Harbor Press, Cold Spring Harbor, N.Y. (1983)] and termination signals derived from bacterial genes such as the trp gene of *E. coli* [Stryer, *Biochemistry*, 2nd ed., W. H. Freeman and Co., San Francisco, Calif. (1981), p. 610].

In another preferred embodiment, the nucleic acid construct further comprises a eukaryotic polyadenylation sequence. The present invention is not limited by the nature of the eukaryotic polyadenylation sequence chosen. In one embodiment, the eukaryotic polyadenylation sequence is selected from the group consisting of the bovine growth hormone polyadenylation sequence, the simian virus 40 polyadenylation sequence and the Herpes simplex virus thymidine kinase polyadenylation sequence. In yet another preferred embodiment, the nucleic acid construct further comprises a selectable marker gene. The present invention is not limited by the nature of the selectable marker gene chosen; the selectable marker may be a positive or negative selectable marker. In a preferred embodiment, the selectable marker is selected from the group consisting of the kanamycin resistance gene, the ampicillin resistance gene, the tetracycline resistance gene, the chloramphenicol resistance gene, the streptomycin resistance gene, the strA gene and the sacB gene.

The present invention is not limited by the nature of the sequence-specific recombinase target site employed on the nucleic acid construct. In one embodiment, the sequence-specific recombinase target site is selected from the group consisting of loxP, loP2, loxP3, loxP23, loxP511, loxB, loxC2, loxL, loxR, loxΔ86, loxΔ117, frt, dif, and att.

In a preferred embodiment, the nucleic construct further comprises a gene of interest inserted into the unique restriction enzyme site.

In a preferred embodiment, the nucleic acid construct has the nucleotide sequence set forth in SEQ ID NO:1 (i.e., pUNI-10).

The present invention further provides a nucleic acid construct comprising, in order 5' to 3': a) a conditional origin of replication; b) a sequence-specific recombinase target site; c) a polylinker; and d) a selectable marker gene. The present invention is not limited by the nature of the polylinker employed. Any collection of two or more restriction enzyme sites which are unique to the nucleic acid construct may be employed as the polylinker. The present invention is not limited by the nature of the conditional origin of replication employed. A variety of conditional origins of replication, including temperature-sensitive replicons are known to the art and may be employed on the nucleic acid constructs of the present invention. In a preferred embodiment, the nucleic acid construct further comprises a prokaryotic termination sequence. The present invention is not limited by the nature of the prokaryotic termination sequence chosen. In one embodiment, the prokaryotic termination sequence is the T7 termination sequence. In another preferred embodiment, the nucleic acid construct further comprises a eukaryotic polyadenylation sequence. The present invention is not limited by the nature of the eukaryotic polyadenylation sequence chosen. In one embodiment, the eukaryotic polyadenylation sequence is selected from the group consisting of the bovine growth hormone polyadenylation sequence, the simian virus 40 polyadenylation sequence and the Herpes simplex virus thymidine kinase polyadenylation sequence. In yet another preferred embodiment, the nucleic acid construct further comprises a selectable marker gene. The present invention is not limited by the nature of the selectable marker gene chosen; the selectable marker may be a positive or negative selectable marker. In a preferred embodiment, the selectable marker is selected from the group consisting of the kanamycin resistance gene, the ampicillin resistance gene, the tetracycline resistance gene, the chloramphenicol resistance gene, the streptomycin resistance gene, the strA gene and the sacB gene.

The present invention is not limited by the nature of the sequence-specific recombinase target site employed on the nucleic acid construct. In one embodiment, the sequence-specific recombinase target site is selected from the group consisting of loxP, loxP2, loxP3, loxP23, loxP511, loxB, loxC2, loxL, loxR, loxΔ86, loxΔ117,frt, dif, and att.

In a preferred embodiment, the nucleic construct further comprises a gene of interest inserted into the polylinker.

The present invention also provides a nucleic acid construct comprising in operable order: a) an origin of replication; b) a promoter element having a 5' and a 3 end; and c) a sequence-specific recombinase target site having a 5' and a 3' end. In a preferred embodiment the 3' end of the promoter element is located upstream of the 5' end of said a sequence-specific recombinase target site. The present invention is not limited by the nature of the origin of replication employed. A variety of non-conditional origins of replication are known to the art and may be employed on the nucleic acid constructs of the present invention. The invention is not limited by the nature of the promoter element employed. Those skilled in the art know that the choice of the promoter element depends upon the type of host cell to be employed for expressing a gene(s) under the transcriptional control of the chosen promoter element. A wide variety of promoter elements functional in prokaryotic (e.g., *E. coli*) and eukaryotic (e.g., yeast, insect, marimals including humans) cells are known to the art and may be employed in the nucleic acid constructs of the present invention.

In another preferred embodiment, the nucleic acid construct further comprises a selectable marker gene. The present invention is not limited by the nature of the selectable marker gene chosen; the selectable marker may be a positive or negative selectable marker. In a preferred embodiment, the selectable marker is selected from the group consisting of the kanamycin resistance gene, the ampicillin resistance gene, the tetracycline resistance gene, the chloramphenicol resistance gene, the streptomycin resistance gene, the strA gene and the sacB gene. The present invention is not limited by the nature of the sequence-specific recombinase target site employed on the nucleic acid construct. In one embodiment, the sequence-specific recombinase target site is selected from the group consisting of loxP, loxP2, loxP3, loxP23, loxP511, loxB, loxC2, loxL, loxR, loxΔ86, loxΔ117, frt, dif and att.

The present invention further provides a nucleic acid construct comprising in operable order: a) a promoter element having a 5' and a 3 end; b) a first sequence-specific recombinase target site having a 5' and a 3' end, wherein the 3' end of the promoter element is located upstream of the 5' end of the a sequence-specific recombinase target site; c) a gene of interest joined to the 3' end of the sequence-specific recombinase target site such that a functional translational reading frame is created; d) a conditional origin of replication; e) a first selectable marker gene; f) a second sequence-specific recombinase target site; and g) an origin of replication. In a preferred embodiment, the first and the second sequence-specific recombinase target site have the same nucleotide sequence (e.g., both comprise a loxP site). The first and the second sequence-specific recombinase target site need not have the same nucleotide sequence provided the different sites can recombine with one another. The present invention is not limited by the nature of either the conditional origin of replication or the non-conditional origin of replication employed.

In a preferred embodiment, the nucleic acid construct further comprises a second selectable marker gene. Preferably the first and the second selectable marker genes are different selectable marker genes. The present invention is not limited by the nature of the selectable marker genes chosen; the selectable marker genes may be positive or negative selectable marker genes. As discussed above, the present invention is not limited by the nature of the promoter element nor the nature of the sequence-specific recombinase target sites chosen.

The present invention also provides a method for the in vitro recombination of nucleic acid constructs, comprising: a) providing: i) a first nucleic acid construct comprising, in operable order, a conditional origin of replication, a first sequence-specific recombinase target site and a first selectable marker gene; ii) a second nucleic acid construct comprising, in operable order, an origin of replication, a promoter element and a second sequence-specific recombinase target site; and iii) a site-specific recombinase; b) contacting the first and the second constructs in vitro with the site-specific recombinase under conditions such that the first and second constructs are recombined to form a third nucleic acid construct.

In a preferred embodiment, the first construct employed in the method further comprises a gene of interest and the recombination of the first and second constructs places the gene of interest under the transcriptional control of the promoter element. In another preferred embodiment, the second construct further comprises a nucleotide sequence encoding an affinity domain and the recombination of the first and second constructs results in placing the gene of interest in frame with the sequence encoding the affinity domain. The present invention is not limited by the nature of the affinity domain employed; a variety of suitable affinity domains are known to the art including glutathione-S-transferase, the maltose binding protein, protein A, polyhistidine tracts, etc.

In a preferred embodiment, the second construct further comprises a second selectable marker gene, the second selectable marker being different from the first selectable marker (present on the first construct). The present invention is not limited by the nature of the selectable marker genes chosen; the selectable marker genes may be positive or negative selectable marker genes. As discussed above, the present invention is not limited by the nature of the promoter element nor the nature of the sequence-specific recombinase target sites chosen.

The present invention further provides a method for the recombination of nucleic acid constructs in a prokaryotic host, comprising: a) providing: i) a first nucleic acid construct comprising a conditional origin of replication, a first sequence-specific recombinase target site having a 5' and a 3' end, a unique restriction enzyme site, the restriction enzyme site located adjacent to the 3' end of the sequence-specific recombinase target site, a first selectable marker gene and a eukaryotic polyadenylation sequence; ii) a second nucleic acid construct comprising an origin of replication, a promoter element having a 5' and a 3' end and a second sequence-specific recombinase target site having a 5' and a 3' end; iii) a procaryotic host cell expressing a site-specific recombinase; b) introducing the first and said second DNA constructs into the prokaryotic host cell under conditions such that the first and second DNA constructs are recombined to form a third nucleic acid construct capable of replicating in the host cell.

In a preferred embodiment, the 3' end of the promoter element is located upstream of the 5' end of the second sequence-specific recombinase target site.

In another preferred embodiment, the method further comprises growing the host cell containing the third construct under conditions which select for the presence of the third construct.

In a preferred embodiment, the first construct further comprises a prokaryotic termination sequence. The present invention is not limited by the nature of the prokaryotic termination sequence chosen. In one embodiment, the prokaryotic termination sequence is the T7 termination sequence.

In another preferred embodiment, the first construct further comprises a gene of interest inserted into the unique restriction endonuclease recognition site.

The present invention also provides a fusion protein comprising protein sequences derived from a glutathione-S-transferase (Gst) protein and a Cre protein; the Gst-Cre fusion protein may be provided in a purified form. In a preferred embodiment, the Gst-Cre fusion protein has the amino acid sequence of SEQ ID NO:11. In another preferred embodiment, the Gst-Cre fusion protein is encoded by the nucleic acid sequence of SEQ ID NO:10.

DESCRIPTION OF THE DRAWINGS

FIG. 8 provides a schematic showing the strategy employed for the in vitro recombination of a pUNI vector ("pA," pUNI-5) with a pHOST vector ("pB," pQL103) to create a fused construct ("pAB"). The relevant markers on each construct are indicated as are selected restriction enzyme sites.

FIG. 9A provides a schematic showing the starting constructs (pUNI-Skp1 and pgst-lox) and the predicted fusion construct (pGst-Skp1) generated by an in vitro fusion reaction.

FIG. 12 provides a schematic illustrating the in vivo gene trap method for the recombination of lox-containing vectors in a host cell constitutively expressing the Cre protein.

FIG. 13 provides the nucleotide sequence of the wild-type loxP site (SEQ ID NO:12), the loxP2 site (SEQ ID NO:13), the loxP3 site (SEQ ID NO:14) and the loxP23 site (SEQ ID NO:15).

DEFINITIONS

Figure 1:
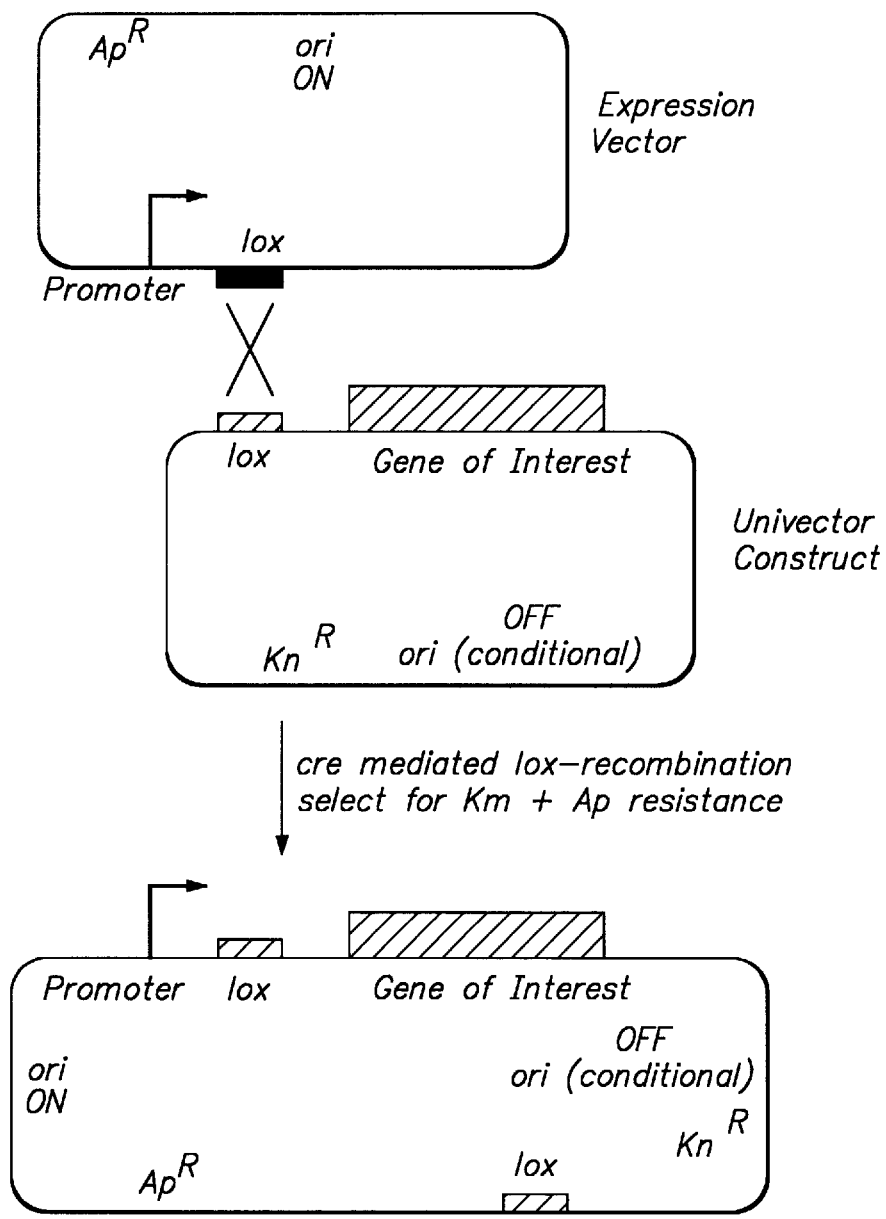
FIG. 1 provides a schematic illustrating certain elements of the pUNI vectors and the Univector Fusion System.

To facilitate understanding of the invention, a number of terms are defined below.

As used herein, "a conditional origin of replication" refers to an origin of replication that requires the presence of a functional trans-acting factor (e.g., a replication factor) in a prokaryotic host cell. Conditional origins of replication encompass temperature-sensitive replicons such as rep pSC101$^{ts}$.

As used herein, the term "origin of replication" refers to an origin of replication that is functional in a broad range of prokaryotic host cells (i.e., a normal or non-conditional origin of replication such as the ColE1 origin and its derivatives).

The terms "sequence-specific recombinase" and "site-specific recombinase" refer to enzymes that recognize and bind to a short nucleic acid site or sequence and catalyze the recombination of nucleic acid in relation to these sites.

The terms "sequence-specific recombinase target site" and "site-specific recombinase target site" refer to short nucleic acid site or sequence which is recognized by a sequence- or site-specific recombinase and which become the crossover regions during the site-specific recombination event. Examples of sequence-specific recombinase target sites include, but are not limited to, lox sites, frt sites, att sites and dif sites.

The term "lox site" as used herein refers to a nucleotide sequence at which the product of the cre gene of bacteriophage P1, Cre recombinase, can catalyze a site-specific recombination. A variety of lox sites are known to the art including the naturally occurring loxP (the sequence found in the P1 genome), loxB, loxL and loxR (these are found in the *E. coli* chromosome) as well as a number of mutant or variant lox sites such as loxP511, loxΔ86, loxΔ117, loxC2, loxP2, loxP3 and loxP23.

The term "frt site" as used herein refers to a nucleotide sequence at which the product of the FLP gene of the yeast 2 μm plasmid, FLP recombinase, can catalyze a site-specific recombination.

The term "unique restriction enzyme site" indicates that the recognition sequence for a given restriction enzyme appears once within a nucleic acid molecule. For example, the EcoRI site is a unique restriction enzyme site within the plasmid pUNI-10 (SEQ ID NO:1).

A restriction enzyme site is said to be located "adjacent to the 3' end of a sequence-specific recombinase target site" if the restriction enzyme recognition site is located downstream of the 3' end of the sequence-specific recombinase target site. The adjacent restriction enzyme site may, but need not, be contiguous with the last or 3' nucleotide comprising the sequence-specific recombinase target site. For example, the EcoRI site of pUNI-10 is located adjacent (within 3 nucleotides) to the 3' end of the loxP site (see FIG. 2B); the XhoI, NdeI, NcoI sites are also adjacent (ie., within about 10–150 nucleotides) to the loxP site but these sites are not contiguous with the 3' end of the loxP site in pUNI-10.

The terms "polylinker" or "multiple cloning site" refer to a cluster of restriction enzyme sites on a nucleic acid construct which are utilized for the insertion and/or excision of nucleic acid sequences such as the coding region of a gene, lox sites, etc.

The term "prokaryotic termination sequence" refers to a nucleic acid sequence which is recognized by the RNA polymerase of a prokaryotic host cell and results in the termination of transcription. Prokaryotic termination sequences commonly comprise a GC-rich region that has a twofold symmetry followed by an AT-rich sequence [Stryer, supra]. A commonly used prokaryotic termination sequence is the T7 termination sequence. A variety of termination sequences are known to the art and may be employed in the nucleic acid constructs of the present invention including, the $T_{INT}$, $T_{L1}$, $T_{L2}$, $T_{L3}$, $T_{R1}$, $T_{R2}$, $T_{6S}$ termination signals derived from the bacteriophage lambda [Lambda II, Hendrix et al. Eds., supra] and termination signals derived from bacterial genes such as the trp gene of *E. coli* [Stryer, supra].

The term "eukaryotic polyadenylation sequence" (also referred to as a "poly A site" or "poly A sequence") as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclII restriction fragment and directs both termination and polyadenylation [J. Sambrook, supra, at 16.6–16.7]; numerous vectors contain the SV40 poly A signal [e.g., pCEP4, pREP4, pEBVHis (Invitrogen)]. Another commonly used heterologous poly A signal is derived from the bovine growth hormone (BGH) gene; the BGH poly A signal is available on a number of commercially available vectors [e.g., pcDNA3.1, pZeoSV2, pSecTag (Invitrogen)]. The poly A signal from the Herpes simplex virus thymidine kinase (HSV tk) gene is also used as a poly A signal on expression vectors; vectors containing the HSV tk poly A signal include the pBK-CMV, pBK-RSV, pOP13CAT vectors from Stratagene.

As used herein, the terms "selectable marker" or "selectable marker gene" refers to the use of a gene which encodes an enzymatic activity that confers the ability to grow in medium lacking what would otherwise be an essential nutrient (e.g., the TRP1 gene in yeast cells); in addition, a selectable marker may confer resistance to an antibiotic or drug upon the cell in which the selectable marker is expressed. A selectable marker may be used to confer a particular phenotype upon a host cell. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene (e.g., the sacB gene which, if expressed, kills the bacterial host cells grown in medium containing 5% sucrose); selectable markers used in this manner are referred to as negative selectable markers or counter-selectable markers.

As used herein, the term "vector" is used in reference to nucleic acid molecules that transfer DNA segment(s) from one cell to another. The term "vehicle" is sometimes used interchangeably with "vector." A "vector" is a type of "nucleic acid construct." The term "nucleic acid construct" includes circular nucleic acid constructs such as plasmid constructs, plasmid constructs, cosmid vectors, etc. as well as linear nucleic acid constructs (e.g., λ phage constructs, PCR products). The nucleic acid construct may comprise expression signals such as a promoter and/or an enhancer (in such a case it is referred to as an expression vector).

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in procaryotes usually include a promoter, an operator (optional), and a ribosome binding site, often along with other sequences. Eucaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "transformation" and "transfection" as used herein refer to the introduction of foreign DNA into prokaryotic or eucaryotic cells. Transformation of prokaryotic cells may be accomplished by a variety of means known to the art including the treatment of host cells with $CaCl_2$ to make competent cells, electroporation, etc. Transfection of eukaryotic cells may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The 3' end of a promoter element is said to be located upstream of the 5' end of a sequence-specific recombinase target site when (moving in a 5' to 3' direction along the nucleic acid molecule) the 3' terminus of a promoter element (the transcription start site is taken as the 3' end of a promoter element) precedes the 5' end of the sequence-specific recombinase target site. The 3' end of the promoter element may be located adjacent (generally within about 0 to 500 bp) to the 5' end of the sequence-specific recombinase target site; such an arrangement is used when the pHOST vector is not intended to permit the expression of a translational fusion with the gene of interest donated by a pUNI vector. Alternatively when the pHOST vector is intended to permit the expression of a translational fusion, the 3' end of the promoter element is located upstream of both the sequences encoding the amino-terminus of a fusion protein and the 5' end of the sequence-specific recombinase target site; in this case, the 5' end of the sequence-specific recombinase target site is located within the coding region of the fusion protein (e.g., located downstream of both the promoter element and the sequences encoding the affinity domain, such as Gst).

As used herein, the term "an oligonucleotide having a nucleotide sequence encoding a gene" means a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription [Maniatis, T. et al., *Science* 236:1237 (1987)]. Promoter and enhancer elements have been isolated from a variety of eucaryotic sources including genes in yeast, insect and mammalian cells and viruses (analogous control elements, i.e., promoters, are also found in procaryotes). The selection of a particular promoter and enhancer depends on what cell type is to be used to express the protein of interest. Some eucaryotic promoters and enhancers have a broad host range while others are functional in a limited subset of cell types [for review see Voss, S.D. et al., *Trends Biochem. Sci.*, 11:287 (1986) and Maniatis, T. et al., supra (1987)]. For example, the SV40 early gene enhancer is very active in a wide variety of cell types from many mammalian species and has been widely used for the expression of proteins in mammalian cells [Dijkema, R. et al., *EMBO J.* 4:761 (1985)]. Two other examples of promoter/enhancer elements active in a broad range of mammalian cell types are those from the human elongation factor 10 gene [Uetsuki, T. et al., *J. Biol. Chem.*, 264:5791 (1989), Kim, D. W. et al., *Gene* 91:217 (1990) and Mizushima, S. and Nagata, S., *Nuc. Acids. Res.*, 18:5322 (1990)] and the long terminal repeats of the Rous sarcoma virus [Gorman, C. M. et al., *Proc. Natl. Acad. Sci. USA* 79:6777 (1982)] and the human cytomegalovirus [Boshart, M. et al., *Cell* 41:521 (1985)].

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site [Sambrook, J. et al., *Molecular Cloning: A Laboratory Manual*, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eucaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene.

Eucaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene and the including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences; these sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "purified" or "to purify" refers to the removal of contaminants from a sample. For example, recombinant Cre polypeptides are expressed in bacterial host cells (as a Gst-Cre fusion protein) and the Cre polypeptides are purified by the removal of host cell proteins; the percent of recombinant Cre polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "fusion protein" refers to a chimeric protein containing the protein of interest (i.e., the Cre protein) joined to an exogenous protein fragment (the fusion partner which consists of non-Cre protein sequences). The fusion partner may enhance solubility of the protein of interest as expressed in a host cell, may provide an affinity tag to allow purification of the recombinant fusion protein from the host cell or culture supernatant, or both. If desired, the fusion protein may be removed from the protein of interest (ie., the Cre protein) by a variety of enzymatic or chemical means known to the art.

DESCRIPTION OF THE INVENTION

The present invention provides reagents and methods which comprise a system for the rapid subcloning of nucleic acid sequences in vivo and in vitro without the need to use restriction enzymes. This system is referred to as the Univector Fusion System. The basis of the Univector Fusion System is a vector termed the Univector or the pUNI vector into which sequences encoding a gene of interest (cDNA or genomic) are inserted. The pUNI vector has a sequence-specific recombinase target site, such as a loxP site, preceding the insertion site for the gene of interest, a selectable marker gene (this feature is optional) and a conditional origin of replication that is active only in host cells expressing the requisite trans-acting replication factor. The pUNI vectors are designed to contain a gene of interest but lack a promoter for the expression of the gene of interest. The gene of interest may be cloned directly into the pUNI vector (i e., the pUNI vector may be used as a cloning vector, particularly for the cloning of cDNA libraries) or a previously cloned gene of interest may be inserted (i.e., subcloned) into the pUNI vector.

Using a sequence-specific recombinase (e.g., Cre recombinase), a precise fusion of the pUNI vector into a second vector containing another copy of the sequence-specific recombinase target site found on the pUNI vector is catalyzed. The second vector, referred to generically as a pHOST vector, is an expression vector that contains the sequence-specific recombinase target site downstream of the promoter element contained within the expression vector. Following the site-specific recombination event which occurs between the single sequence-specific recombinase target sites located on each vector (e.g., the pUNI vector and the pHOST vector), the two vectors are stably fused in a manner that places the expression of the gene of interest under the control of the promoter element contained within the expression vector. This fusion event also occurs in a manner that retains the proper translational reading frame of the gene of interest. This subcloning event occurs without the need to use restriction enzymes.

The fusion or recombination event can be selected for by selecting for the ability of host cells, which do not express the trans-acting replication factor required for replication of the conditional origin contained on the pUNI vector, to acquire the selectable phenotype conferred by the selectable marker gene (if present) on the pUNI vector. The pUNI vector cannot replicate in cells that do not express the trans-acting replication factor and therefore, unless the pUNI vector has integrated into the second vector that contains a non-conditional origin of replication, pUNI will be lost from the host cell.

The Univector Fusion System allows any number of expression constructs containing the gene of interest present on the pUNI vector to be made rapidly (e.g., within a single day). Using conventional cloning or subcloning techniques which employ restriction enzyme digestion(s), the production of a single expression vector containing a gene of interest can take several days (for the design and construction of each expression vector). In contrast, once a battery of expression vectors modified to contain the appropriate sequence-specific recombinase target site is made, a gene of interest can be transferred to any number of expression vectors in an afternoon using the Univector Fusion System.

FIG. 1 provides a schematic illustrating certain elements of the pUNI vectors and the Univector Fusion System.

a) Conditional Origins of Replication and Suitable Host Cells

Conditional origins of replication are origins which require the presence or expression of a trans-acting factor in the host cell for replication. A variety of conditional origins of replication functional in prokaryotic hosts (e.g., *E. coli*) are known to the art. The present invention is illustrated but not limited by the use of the R6Kγ origin, oriR, from the plasmid R6K. The R6Kγ origin requires a trans-acting factor, the II protein supplied by the pir gene [Metcalf et al. (1996) Plasmid 35:1]. *E. coli* strains containing the pir gene will support replication of R6Kγ origins to medium copy number. A strain containing a mutant allele of pir, pir-116, will allow an even higher copy number of constructs containing the R6Kγ origin.

*E. coli* strains that express the pir or pir- 116 gene product include BW18815 (ATCC 47079; this strain contains the pir-116 gene), BW19094 (ATCC 47080; this strain contains the pri gene), BW20978 (this strain contains the pir-116 gene), BW20979 (this strain contains the pir gene), BW21037 (this strain contains the pir-116 gene) and BW21038 (this strain contains the pir gene) (Metcalf et al, supra).

Other conditional origins of replication suitable for use on the pUNI vectors of the present invention include:

1) the RK2 oriV from the plasmid RK2 (ATCC 37125). The RK2 oriV requires a trans-acting protein encoded by the trfA gene [Ayres et al. (1993) J. Mol. Biol. 230:174];

2) the bacteriophage P1 ori which requires the repA protein for replication [Pal et al. (1986) J. Mol. Biol. 192:275];

3) the origin of replication of the plasmid pSC101 (ATCC 37032) which requires a plasmid encoded protein, repA, for replication [Sugiura et al. (1992) J. Bacteriol. 175: 5993]. The pSC101 ori also requires IHF, an *E. coli* protein. *E. coli* strains carrying the himA and himD (hip) mutants (the him and hip genes encode subunits of IHF) cannot support pSC101 replication [Stenzel et al. (1987) Cell 49:709];

4) the bacteriophage lambda ori which requires the lambda O and P proteins [Lambda II, Hendrix et al. Eds., Cold Spring Harbor Press, Cold Spring Harbor, N.Y. (1983)];

5) pBR322 and other ColEI derivatives will not replicate in polA mutants of *E. coli* and therefore, these origins of replication and be used in a conditional manner [Grindley and Kelley (1976) Mol. Gen. Genet. 143:311]; and 6) replication-thermosensitive plasmids such pSU739 or pSU300 which contain a thermosensitive replicon derived from plasmid pSC101, rep pSC101$^{ts}$ which comprises oriV [Mendiola and de la Cruz (1989) Mol. Microbiol. 3:979 and Francia and Lobo (1996) J. Bact. 178:894]. pSU739 and pSU300 are stably maintained in *E. coli* strain DH5α (Gibco BRL) at a growth temperature of 30° C. (42° C. is non-permissive for replication of this replicon).

Other conditional origins of replication, including other temperature sensitive replicons, are known to the art and may be employed in the vectors and methods of the present invention.

b) Sequence-Specific Recombinases And Target Recognition Sites

The precise fusion between the pUNI vector and the expression vector is catalyzed by a site-specific recombinase. Site-specific recombinases are enzymes that recognize a specific DNA site or sequence (referred to herein generically as a "sequence-specific recombinase target site") and catalyzes the recombination of DNA in relation to these sites. Site-specific recombinases are employed for the recombination of DNA in both prokaryotes and eukaryotes. Examples of site-specific recombination include 1) chromosomal rearrangements which occur in *Salmonella typhimurium* during phase variation, inversion of the FLP sequence during the replication of the yeast 2 μm circle and in the rearrangement of immunoglobulin and T cell receptor genes in vertebrates, 2) integration of bacteriophages into the chromosome of prokaryotic host cells to form a lysogen and 3) transposition of mobile genetic elements (e.g., transposons) in both prokaryotes and eukaryotes. The term "site-specific recombinase" refers to enzymes that recognize short DNA sequences that become the crossover regions during the recombination event and includes recombinases, transposases and integrases.

The present invention is illustrated but not limited by the use of vectors containing loxP sites and the recombination of these vectors using the Cre recombinase of bacteriophage P1. The Cre protein catalyzes recombination of DNA between two loxP sites [Sternberg et al. (1981) Cold Spring Harbor Symp. Quant. Biol. 45:297]. The loxP sites may be present on the same DNA molecule or they may be present on different DNA molecules; the DNA molecules may be linear or circular or a combination of both. The loxP site consists of a double-stranded 34 bp sequence (SEQ ID NO:12) which comprises two 13 bp inverted repeat sequences separated by an 8 bp spacer region [Hoess et al. (1982) Proc. Natl. Acad. Sci. USA 79:3398 and U.S. Pat. No. 4,959,317, the disclosure of which is herein incorporated by reference]. The internal spacer sequence of the loxP site is asymmetrical and thus, two loxP sites can exhibit directionality relative to one another [Hoess et al. (1984) Proc. Natl. Acad. Sci. USA 81:1026]. When two loxP sites on the same DNA molecule are in a directly repeated orientation, Cre excises the DNA between these two sites leaving a single loxP site on the DNA molecule [Abremski et al. (1983) Cell 32:1301]. If two loxP sites are in opposite orientation on a single DNA molecule, Cre inverts the DNA sequence between these two sites rather than removing the sequence. Two circular DNA molecules each containing a single loxP site will recombine with another to form a mixture of monomer, dimer, trimer, etc. circles. The concentration of the DNA circles in the reaction can be used to favor the formation of monomer (lower concentration) or multimeric circles (higher concentration).

Circular DNA molecules having a single loxP site will recombine with a linear molecule having a single loxP site to produce a larger linear molecule. Cre interacts with a linear molecule containing two directly repeating loxP sites to produce a circle containing the sequences between the loxP sites and a single loxP site and a linear molecule containing a single loxP site at the site of the deletion.

The Cre protein has been purified to homogeneity [Abremski et al. (1984) J. Mol. Biol. 259:1509] and the cre gene has been cloned and expressed in a variety of host cells [Abremski et al. (1983), supra]. Purified Cre protein is available from a number of suppliers (e.g., Novagen and New England Nuclear/Du Pont).

The Cre protein also recognizes a number of variant or mutant lox sites (variant relative to the loxP sequence), including the loxB, loxL and loxR sites which are found in the E. coli chromosome [Hoess et al. (1982), supra]. Other variant lox sites include loxP511 [5'-ATAACTTCGTATA GTATACATTATACGAAGTTAT-3' (SEQ ID NO:16); spacer region underlined; Hoess et al. (1986), supra], loxC2 [5'-ACAAC TTCGTATA ATGTATGCTATACGAAGTTAT-3' (SEQ ID NO:17); spacer region underlined; U.S. Pat. No. 4,959,317). Cre catalyzes the cleavage of the lox site within the spacer region and creates a six base-pair staggered cut [Hoess and Abremski (1985) J. Mol. Biol. 181:351]. The two 13 bp inverted repeat domains of the lox site represent binding sites for the Cre protein. If two lox sites differ in their spacer regions in such a manner that the overhanging ends of the cleaved DNA cannot reanneal with one another, Cre cannot efficiently catalyze a recombination event using the two different lox sites. For example, it has been reported that Cre cannot recombine (at least not efficiently) a loxP site and a loxP511 site; these two lox sites differ in the spacer region. Two lox sites which differ due to variations in the binding sites (ie., the 13 bp inverted repeats) may be recombined by Cre provided that Cre can bind to each of the variant binding sites; the efficiency of the reaction between two different lox sites (varying in the binding sites) may be less efficient that between two lox sites having the same sequence (the efficiency will depend on the degree and the location of the variations in the binding sites). For example, the loxC2 site can be efficiently recombined with the loxP site; these two lox sites differ by a single nucleotide in the left binding site.

A variety of other site-specific recombinases may be employed in the methods of the present invention in place of the Cre recombinase. Alternative site-specific recombinases include:

1) the FLP recombinase of the 2pi plasmid of Saccharomyces cerevisiae [Cox (1983) Proc. Natl. Acad. Sci. USA 80:4223] which recognize the frt site which, like the loxP site, comprises two 13 bp inverted repeats separated by an 8 bp spacer [5'-GAAGTTCCTATTCTCTAGAAAGT ATAGGAACTTC-3'(SEQ ID NO:18); spacer underlined]. The FLP gene has been cloned and expressed in E. coli (Cox, supra) and in mammalian cells (PCT International Patent Application PCTIUS92/01899, Publication No.: WO 92/15694, the disclosure of which is herein incorporated by reference) and has been purified [Meyer-Lean et al. (1987) Nucleic Acids Res. 15:6469; Babineau et al (1985) J. Biol. Chem. 260:12313; Gronostajski and Sadowski (1985) J. Biol. Chem. 260:12328];

2) the Int recombinase of bacteriophage lambda (with or without Xis) which recognizes att sites (Weisberg et al. In: Lambda II, supra, pp. 211–250);

3) the xerC and xerD recombinases of E. coli which together form a recombinase that recognizes the 28 bp dif site [Leslie and Sherratt (1995) EMBO J. 14:1561];

4) the Int protein from the conjugative transposon Tn916 [Lu and Churchward (1994) EMBO J. 13:1541];

5) TpnI and the β-lactamase transposons [Levesque (1990) J. Bacteriol. 172:3745];

6) the Tn3 resolvase [Flanagan et al. (1989) J. Mol. Biol. 206:295 and Stark et al. (1989) Cell 58:779];

7) the SpoIVC recombinase of Bacillus subtilis [Sato et al. J. Bacteriol. 172:1092];

8) the Hin recombinase [Galsgow et al. (1989) J. Biol. Chem. 264:10072];

9) the Cin recombinase [Hafter et al. (1988) EMBO J. 7:3991]; and 10) the immunoglobulin recombinases [Malynn et al. Cell (1988) 54:453].

c) Modification of Expression Vectors

As discussed above, pUNI vectors are used to transfer a gene of interest into a suitably modified expression vector via site-specific recombination. The modified expression vectors or host vectors used in the Univector Fusion System are referred to as pHOST vectors. pHOST vectors are generally expression vectors (e.g., plasmids) which have been modified by the insertion of a sequence-specific recombinase target site (e.g., a lox site). The presence of the sequence-specific recombinase target site on the pHOST plasmid permits the rapid subcloning or insertion of the gene interest contained within a pUNI vector to generate an expression vector capable of expressing the gene of interest. The pHOST vector may encode a protein domain such as an affinity domain including, but not limited to, glutathione-S-transferase (Gst), maltose binding protein (MBP), a portion of staphylococcal protein A (SPA), a polyhistidine tract, etc. A variety of commercially available expression vectors encoding such affinity domains are known to the art. The affinity domain may be located at either the amino- or carboxy-terminus of the fusion protein. When the pHOST plasmid contains a vector-encoded affinity domain, a fusion protein comprising the vector-encoded affinity domain and the protein of interest is generated when the pUNI and pHOST vectors are recombined.

To generate expression vectors intended to generate transcriptional fusions (i.e., pHOST does not contain a vector-encoded protein domain), a sequence-specific recombinase target site is placed after (i.e., downstream of) the start of transcription in the host vector; this is easily accomplished using synthetic oligonucleotides comprising the desired sequence-specific recombinase target site. In designing the oligonucleotide comprising the sequence-specific recombinase target site, care is taken to avoid introducing an ATG or start codon that might initiate translation inappropriately.

To generate expression vectors intended to generate a fusion protein between a vector-encoded protein domain located at the amino-terminus of the fusion protein and the protein of interest (encoded by the gene of interest contained within the pUNI vector) (i.e., a translational fusion), care is taken to place the sequence-specific recombinase target site in the correct reading frame such that 1) an open reading frame is maintained through the sequence-specific recombinase target site on pHOST and 2) the reading frame in the sequence-specific recombinase target site on pHOST is in frame with the reading frame found on the sequence-specific recombinase target site contained within the pUNI vector. In addition, the oligonucleotide comprising the sequence-specific recombinase target site on pHOST is designed to avoid the introduction of in-frame stop codons. The gene of interest contained within the pUNI vector is cloned in a particular reading frame so as to facilitate the creation of the desired fusion protein.

The modification of several expression vectors is provided in the examples below to illustrate the creation of suitable pHOST vectors. The general strategy involves the generation of a linker containing the desired sequence-specific recombinase target site (e.g., a lox site) by annealing two complementary oligonucleotides. The annealed oligonucleotides form a linker having sticky ends which are compatible with ends generated by restriction enzymes whose sites are conveniently located in the parental expression vector (e.g., within the polylinker of the parental expression vector).

d) In Vitro Recombination

The fusion of a pUNI vector and a pHOST vector may be accomplished in vitro using a purified preparation of a site-specific recombinase (e.g., Cre recombinase). The pUNI vector and the pHOST vector are placed in reaction vessel (e.g., a microcentrifuge tube) in a buffer compatible with the site-specific recombinase to be used. For example, when a Cre recombinase (native or a fusion protein form) is employed, the reaction buffer may comprise 50 mM Tris-HCl (pH 7.5), 10 mM $MgCl_2$, 30 mM NaCl and 1 mg/ml BSA. When a FLP recombinase is employed, the reaction buffer may comprise 50 mM Tris-HCl (pH 7.4), 10 mM $MgCl_2$, 100 µg/ml BSA [Gronostajski and Sadowski (1985) 260:12320]. The concentration of the pUNI vector and the pHOST vector may vary between 100 ng to 1.0 µg of each vector per 20 µl reaction volume with about 0.1 µg of each nucleic acid construct (0.2 µg total) per 20 µl reaction being preferred. The concentration of the site-specific recombinase may be titered under a standard set of reaction conditions to find the optimal concentration of enzyme to be used as described in Ex. 4.

Following the in vitro fusion reaction, a portion of the reaction mixture is used to transform a suitable host cell to permit the recovery and propagation of the fused vectors. The host cell employed will not express the trans-acting factor required for replication of the conditional origin of replication contained within the pUNI vector (or alternatively the host cell will be grown at a temperature which is non-permissive for replication of a temperature sensitive replicon contained within the pUNI vector). The host cells will be grown under conditions which select for the presence of the selectable marker contained within the pUNI vector (e.g., growth in the presence of kanamycin when the pUNI vector contains the kanamycin resistance gene). Plasmid or non-chromosomal DNA is isolated from host cells which display the desired phenotype and subjected to restriction enzyme digestion to confirm that the desired fusion event has occurred.

e) Recombination in Procaryotic Host Cells

The fusion of a pUNI vector and a pHOST vector may be accomplished in vivo using a host cell that expresses the appropriate site-specific recombinase (e.g., Cre recombinase). The host cell employed will lack the ability to express the trans-acting factor required for replication of the conditional origin of replication contained within the pUNI vector (or alternatively the host cell will be grown at a temperature which is non-permissive for replication of a temperature sensitive replicon contained within the pUNI vector).

The pUNI vector and the pHOST vector are cotransformed into the host cell using a variety of methods known to the art (e.g., transformation of cells made competent by treatment with $CaCl_2$, electroporation, etc.). The cotransformed host cells are grown under conditions which select for the presence of the selectable marker contained within the pUNI vector (e.g., growth in the presence of kanamycin when the pUNI vector contains the kanamycin resistance gene). Plasmid or non-chromosomal DNA is isolated from host cells which display the desired phenotype and subjected to restriction enzyme digestion to confirm that the desired fusion event has occurred.

In addition to permitting the rapid transfer of a gene of interest from a particular pUNI vector containing a gene of interest into a pHOST vector, the Univector Fusion System permits the rapid exchange of an entire cDNA library to a variety of expression vectors. The cDNA library is generated using a pUNI vector as the cloning vector (a pUNI library). The entire library may then be transferred (using either an in vitro or an in vivo recombination reaction) into any expression vector modified to contain a sequence-specific recombinase target site (e.g., a lox site) (i.e., into a pHOST vector). This solves an existing problem in the art, in that there is no way, using existing vector systems, to exchange the inserts in a library made in one expression vector en masse (i.e., as an entire library) to a different expression vector. In addition, the sequences contained within a pUNI library can be used to recombine with linear λ constructs (which can then be used to isolate specific genes by complementation of an appropriate host cells such as E. coli or S. cerevisiae mutant cells). Further as described in Example 8, the in vivo gene trap method, a variation of the Univector Fusion System, can be used to transfer linear DNA fragments that lack a selectable marker such as a PCR product into a variety of expression vectors.

EXPERIMENTAL

The following examples serve to illustrate certain preferred embodiments and aspects of the present invention and are not to be construed as limiting the scope thereof.

In the experimental disclosure which follows, the following abbreviations apply: °C. (degrees Centigrade); g (gravitational field); vol (volume); DNA (deoxyribonucleic acid); RNA (ribonucleic acid); kdal or kD (kilodaltons); OD (optical density); EDTA (ethylene diamine tetra-acetic acid); E. coli (Escherichia coli); SDS (sodium dodecyl sulfate); PAGE (polyacrylamide gel electrophoresis); p (plasmid); LB (Luria-Bertani medium: per liter: 10 g Bacto-tryptone, 5 g yeast extract, 10 g NaCl, pH to 7.5 with NaOH); ml (milliliter); μl (microliter); M (Molar); mM (millimolar); μM (microMolar); g (gram); μg (microgram); ng (nanogram); U (units), mU (milliunits); min. (minutes); sec. (seconds); % (percent); bp (base pair); kb (kilobase); PCR (polymerase chain reaction); Tris (tris(hydroxymethyl)-aminomethane); PMSF (phenylmethylsulfonylfluoride); BSA (bovine serum albumin); IPTG (isopropyl-β-D-thiogalactoside); ATCC (American Type Culture Collection, Rockville, Md.); Bio-Rad (Bio-Rad Corp., Hercules, Calif.); Invitrogen (Invitrogen, Corp., San Diego, Calif.); New England Nuclear/Du Pont (Boston, Mass.); Novagen (Novagen, Inc., Madison, Wis.); Pharmacia or Pharmacia Biotech (Pharmacia Biotech, Piscataway, N.J.); Pharmingen (PharMingen, San Diegi, Calif.); Gibco BRL (Gaithersburg, Md.); and Stratagene (Stratagene Cloning Systems, La Jolla, Calif.).

EXAMPLE 1

Construction Of Univector Constructs

In this example, an illustrative Univector construct is provided, the pUNI-10 vector, which contains a loxP site, a kanamycin resistance gene (Kn®) and the R6Kγ conditional origin of replication (OriR$_{R6K\gamma}$). The OriR$_{R6K\gamma}$ is functional only in E. coli strains expressing the II replication protein (i.e., the product of the pir gene). A gene of interest is placed within pUNI-10 (either as a result of constructing a library in pUNI-10 or by subcloning a previously cloned gene of interest). Once the gene of interest is contained within pUNI-10, any number of plasmid expression constructs containing this gene of interest can be constructed rapidly (e.g., within a single day). The expression constructs will contain an antibiotic resistance gene other than kanamycin (e.g., ampicillin). Using the site-specific recombinase, Cre, a precise fusion between the pUNI vector and any other loxP site-containing vector comprising the desired expression signals adjacent to the loxP site is catalyzed. The site-specific recombination event which occurs between the single loxP sites located on each plasmid (e.g., pUNI and the expression vector) results in the stable fusion of these two plasmids in such a manner as to place the expression of the gene of interest under the control of the expression signals contained within the expression vector. This subcloning event occurs without the need to use restriction enzymes. The fusion of pUNI-10 and the expression vector is selected for by selecting for the ability of E. coli cells that do not express the II protein to grow in the presence of kanamycin. pUNI cannot replicate in E. coli cells that do not express the II protein unless pUNI has fused or integrated into another plasmid that contains a normal (i.e., not a conditional) origin of replication (e.g., the Col El origin); in this case, pUNI will be replicated (as part of the fusion plasmid) and kanamycin resistance will be conferred on the host cell.

a) Generation of pUNI-10

Figures 2A, 2B:
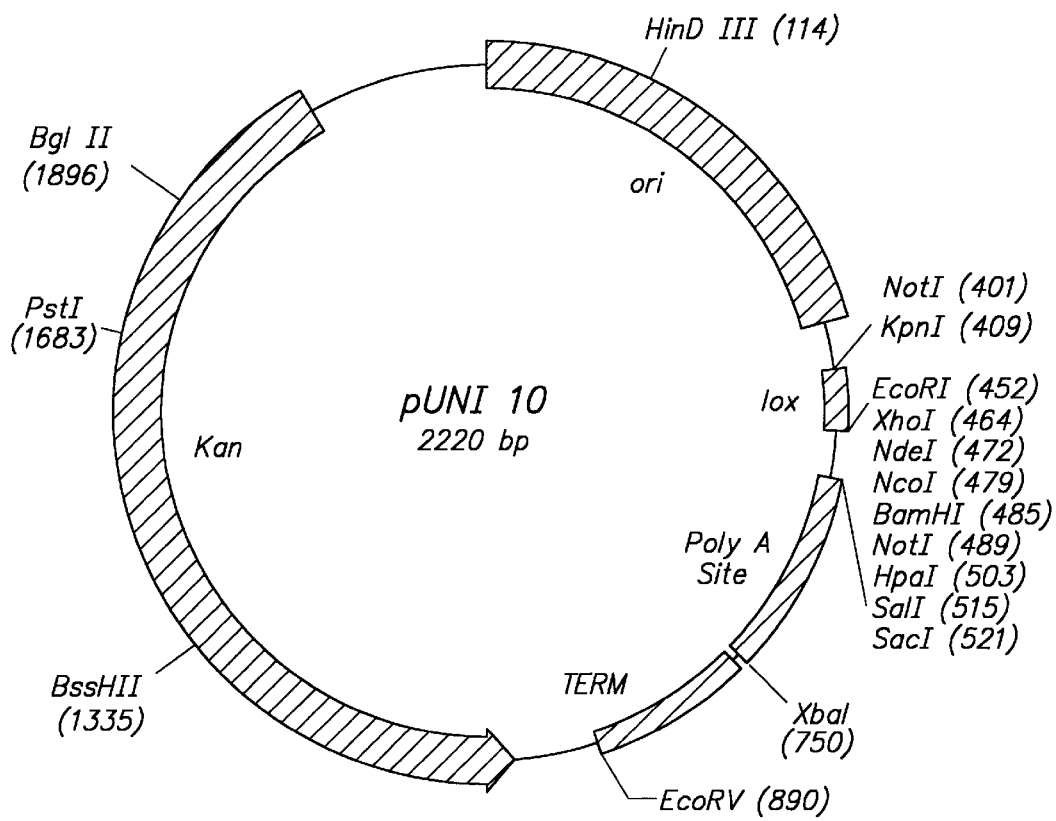
FIG. 2A provides a schematic map of the pUNI-10 vector; the locations of selected restriction enzyme sites are indicated and unique sites are indicated by the use of bold type.
FIG. 2B shows the DNA sequence of the loxP site and the polylinkers contained within pUNI-10 (i.e., nucleotides 401–530 of SEQ ID NO:1).

FIG. 2A provides a schematic map of the pUNI-10 vector; the locations of selected restriction enzyme sites are indicated (with the exception of NotI, all sites shown are unique). FIG. 2B shows the DNA sequence of the loxP site and the polylinkers contained within pUNI-10 (i.e., nucleotides 401–530 of SEQ ID NO:1).

Nucleotides 1–400 of pUNI-10 contain the conditional origin of replication from R6Kγ (OriR$_{R6K\gamma}$); the OriR$_{R6K\gamma}$ was derived from the plasmid R6K (ATCC 37120) [Metcalf et al. (1996) Plasmid 35:1]; nucleotides 401–414 comprise a NotI-KpnI polylinker that facilitates the exchange of lox sites; pUNI-10 contains a wild-type loxP site (as discussed above, pUNI vectors containing modified lox sites may be employed). Nucleotides 415–448 comprise the wild-type loxP site; nucleotides 449–527 comprise a polylinker used for the insertion of the gene of interest (genomic or cDNA sequences). Nucleotides 528–750 contain the polyA addition sequence from bovine growth hormone (BGH) [the BGH polyA sequence is available on a number of commercially available vectors including pcDNA3.1 (Invitrogen)]; the BGH polyA sequence is provides a 3' end for transcripts expressed in mammalian and other eukaryotic cells. The art is aware of other eukaryotic polyA sequences which may be used in place of the BGH polyA sequence (e.g., the SV40 poly A sequence, the TK polyA sequence, etc.). Nucleotides 751–890 contain the T7 terminator sequence which is used to terminate transcription in prokaryotic hosts (numerous prokaryotic termination signals are known to the art and may be employed in place of the T7 terminator sequence). Nucleotides 890–895 comprise an EcoRV restriction enzyme recognition site and nucleotides 896–2220 comprise the kanamycin resistance gene (Kan or Kn®) from Tn5 which provides a positive selectable marker. The Kn$^R$ gene found on pUNI-10 was modified using site-directed mutagenesis to remove the naturally occurring NcoI site such that pUNI-10 contains a unique NcoI site in the polylinker region located at nucleotides 449–527. pUNI vectors need not contain a Kn® gene (modified or wild-type); other selectable genes may be used in place of the Kn® gene (e.g., ampicillin resistance gene, tetracycline resistance gene, zeocin™ resistance gene, etc.). The pUNI vector need not contain a selectable marker, although the use of a selectable marker is preferred. When a selectable marker is present on the pUNI vector, this marker is preferably a different selectable marker than that present on the pHOST vector.

The nucleotide sequence of pUNI-10 is provided in SEQ ID NO:1.

EXAMPLE 2

Construction Of Host Plasmids For Use In The Univector Plasmid-Fusion System Host plasmids used in the Univector plasmid fusion system are referred to as pHOST plasmids. pHOST plasmids or vectors are generally expression vectors which have been modified by the insertion of a lox site. The presence of the lox site on the pHOST plasmid permits the rapid subcloning or insertion of the gene interest contained within a pUNI vector to generate an expression vector capable of expressing the gene of interest. The pHOST vector may encode a protein domain such as an affinity domain including, but not limited to, glutathione-S-transferase (Gst), maltose binding protein (MBP), a portion of staphylococcal protein A (SPA), a polyhistidine tract, etc. A variety of commercially available expression vectors encoding such affinity domains are known to the art. When the pHOST plasmid contains a vector-encoded affinity domain, a fusion protein comprising the vector-encoded affinity domain and the protein of interest is generated when the pUNI and pHOST vectors are recombined.

To generate expression vectors intended to generate transcriptional fusions (i.e., pHOST does not contain a vector-encoded protein domain), a lox site is placed after (i.e., downstream of) the start of transcription in the host vector; this is easily accomplished using synthetic oligonucleotides comprising the desired lox site. In designing the oligonucleotide comprising the lox site, care is taken to avoid introducing an ATG or start codon that might initiate translation inappropriately.

To generate expression vectors intended to generate a fusion protein between a vector-encoded protein domain and the protein of interest (encoded by the gene of interest contained within the pUNI vector), care is taken to place the lox site in the correct reading frame such that 1) an open reading frame is maintained through the lox site on pHOST and 2) the reading frame in the lox site on pHOST is in frame with the reading frame found on the lox site contained within the pUNI vector. In addition, the oligonucleotide comprising the lox site on pHOST is designed to avoid the introduction of in-frame stop codons. The gene of interest contained within the pUNI vector is cloned in a particular reading frame so as to facilitate the creation of the desired fusion protein.

The modification of several expression vectors is provided below to illustrate the creation of suitable pHOST vectors. In each case, the general strategy involved the generation of a linker containing a lox site by annealing two complementary oligonucleotides. The annealed oligonucleotides form a linker having sticky ends which are compatible with ends generated by restriction enzymes whose sites are conveniently located in the parental expression vector (e.g., within the polylinker of the parental expression vector).

a) Modification of the pGEX-2TKcs Procaryotic Expression Vector pGEX-2TKcs is an expression vector active in E. coli cells which is designed for inducible, intracellular expression of genes or gene fragments as fusions with Gst. pGEX-2TKcs contains the IPTG-inducible tac promoter ($P_{tac}$) and was derived from pGEX-2TK (Pharmacia Biotech) as follows. The polylinker sequence of pGEX-2TK, 5'-GGATCCCCGGGAATTC-3' (SEQ ID NO:2), was replaced with the following sequence: 5'-GGAT CGCATATGCCCATGGCTCGAGGATCCGAATTC-3' (SEQ ID NO:3) to generate the pGEX-2TKcs vector.

Figure 3:
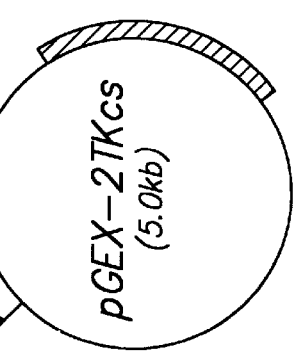
FIG. 3A shows the oligonucleotides (SEQ ID NOS:4 and 5) which were annealed to insert a loxP site into the polylinker of pGEX-2TKcs to create pgst-lox.
FIG. 3B provides a schematic map of pGEX-2TKcs which includes an enlargement of the multiple cloning site (MCS).
Figure 4:
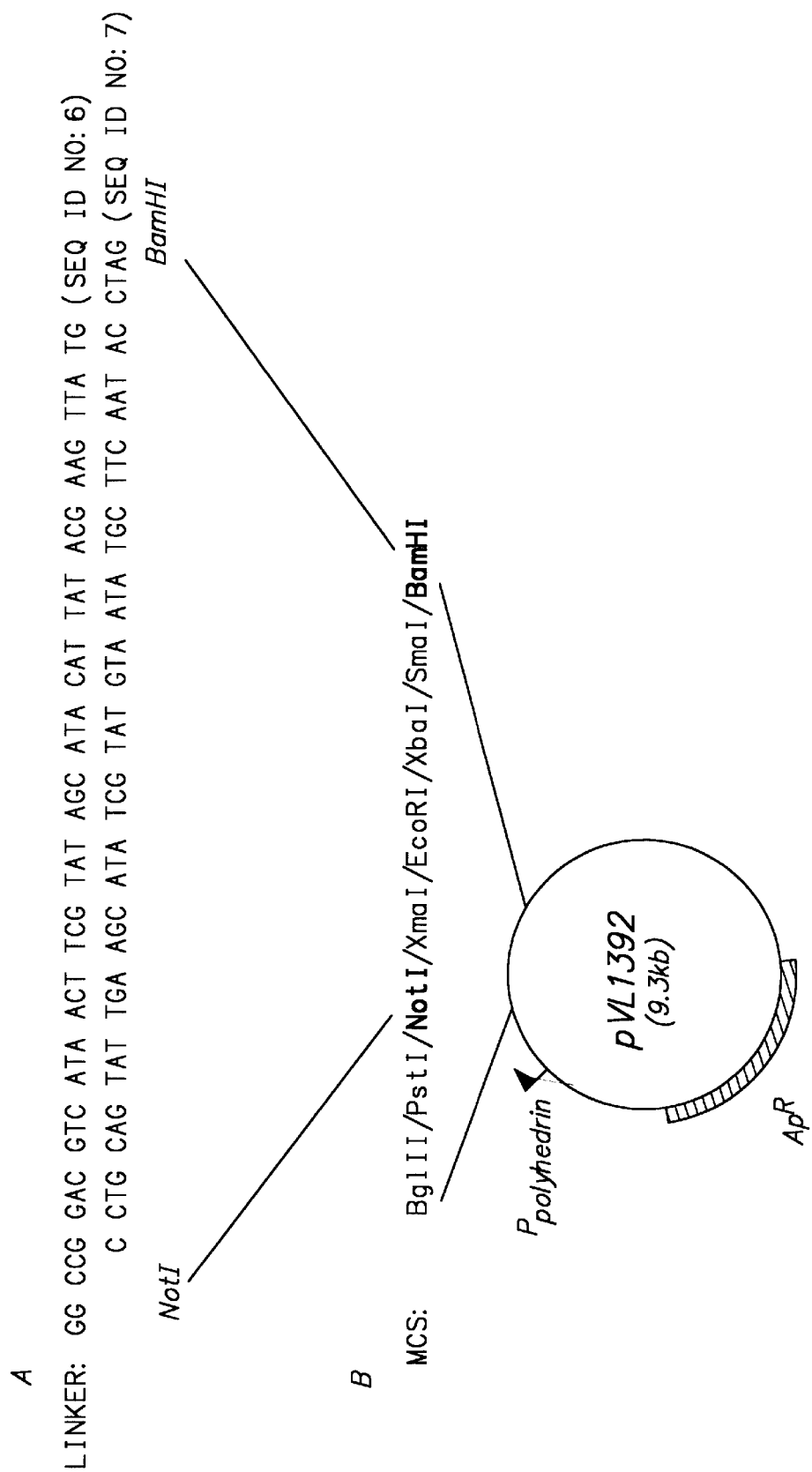
FIG. 4A shows the oligonucleotides (SEQ ID NOS:6 and 7) which were annealed to insert a loxP site into the polylinker of pVL1392 to create pVL1392-lox.
FIG. 4B provides a schematic map of pVL1392 which includes an enlargement of the multiple cloning site (MCS); the ampicillin resistance gene (Ap®) and the tac promoter ($P_{tac}$) are indicated.
Figure 5:
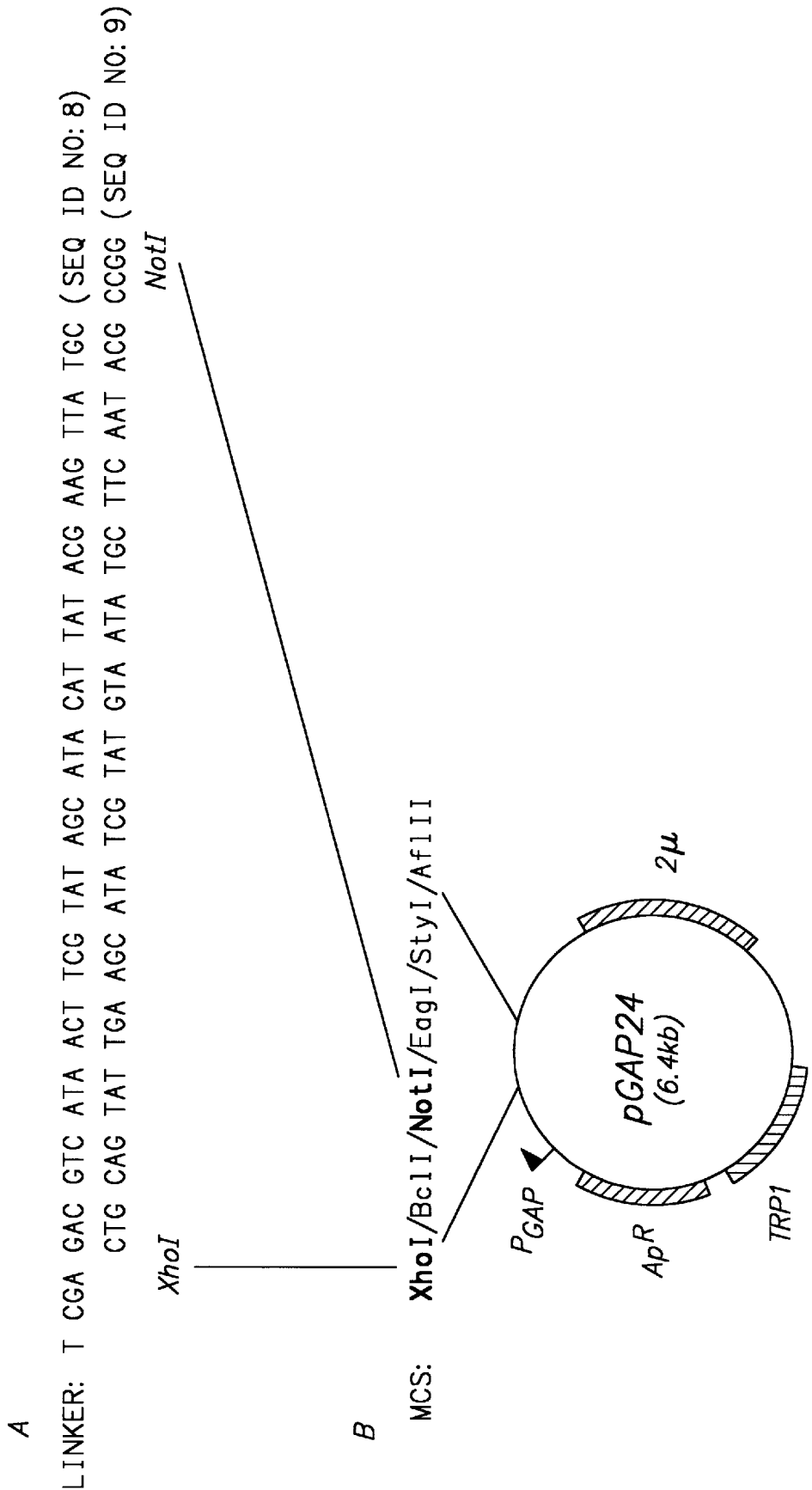
FIG. 5A shows the oligonucleotides (SEQ ID NOS:8 and 9) which were annealed to insert a loxP site into the polylinker of pGAP24 to create pGAP24-lox.
FIG. 5B provides a schematic map of pGAP24 which includes an enlargement of the multiple cloning site (MCS); the ampicillin resistance gene (Ap®), the GAP promoter ($P_{GAP}$), the origin from the 2 μm circle (2μ) and the TRP1 gene, encoding N-(5'-phosphoribosyl)-anthranilate synthetase, (TRP1) are indicated.
Figure 6:
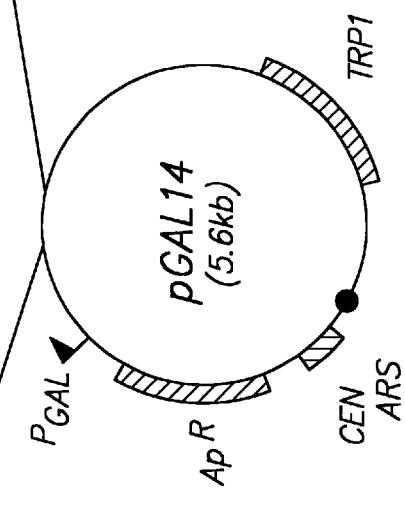
FIG. 6A shows the oligonucleotides (SEQ ID NOS:8 and 9) which were annealed to insert a loxP site into the polylinker of pGAL14 to create pGAL14-lox.
FIG. 6B provides a schematic map of pGAL14 which includes an enlargement of the multiple cloning site (MCS); the ampicillin resistance gene (Ap®), the GAL promoter ($P_{GAL}$), the yeast centromeric sequences (CEN), yeast autonomous replication sequences (ARS) and the TRP1 gene (TRP1) are indicated.

A linker containing a loxP site was generated by annealing the following oligonucleotides: 5 '-CATGGCTATAACT TCGTATAGCATACATTATACGAA GTTATG-3' (SEQ ID NO:4) and 5'-GATCCATAACTTCGTATAATGTATGC TATACGAAGTTATAGC-3' (SEQ ID NO:5). When annealed, these two oligonucleotides form a double-stranded linker having a 5' end compatible with an NcoI sticky end and a 3' end compatible with a BamHI sticky end (FIG. 3A). pGEX-2TKcs was digested with NcoI and BamHI (FIG. 3B) and the annealed loxP linker was inserted to form pgst-lox.

b) Modification of the pVL1392 Baculovirus Expression Vector pVL1392 is an expression vector that contains the polyhedrin promoter which is active in insect cells (Pharmingen). A linker containing a loxP site was generated by annealing the following oligonucleotides: 5'-GGCCGGACGTCATAACTTCGTAT AGCATACATTATACGAAGTTATG-3' (SEQ ID NO:6) and 5'-GATCCATAACTTC GTATAATGTATGCTATACG AAGTTATGACGTCC-3' (SEQ ID NO:7). When annealed, these two oligonucleotides form a double-stranded linker having a 5' end compatible with a NotI sticky end and a 3' end compatible with a BamHI sticky end (FIG. 4A). pVL1392 was digested with NotI and BamHI (FIG. 4B) and the annealed loxP linker was inserted to form pVL1392-lox.

c) Modification of the pGAP24 Yeast Expression Vector pGAP24 is an expression vector that is based on the yeast 2 μm circle and contains the constitutive GAP (glyceraldehyde 3-phosphate dehydrogenase) promoter ($P_{GAP}$) which is active in yeast cells and the TRP1 gene (used a selectable marker when the cells are grown in medium lacking tryptophan) [the GAP promoter is available on pAB23; Schilds (1990) Proc. Natl. Acad. Sci. USA 87:2916]. A linker containing a loxP site was generated by annealing the following oligonucleotides: 5'-TCGAGAC GTCATAACTTCGTATAGCATACATTATACGAAGTTA TGC-3' (SEQ ID NO:8) and 5'-GGCCGCATAACTTCGTA TAATGTATGCTATACGAAGTTATGACGTC-3' (SEQ ID NO:9). When annealed, these two oligonucleotides form a double-stranded linker having a 5' end compatible with a XhoI sticky end and a 3' end compatible with a NotI sticky end (FIG. 5A). pGAP24 was digested with XhoI and NotI (FIG. 5B) and the annealed loxP linker was inserted to form pGAP24-lox.

d) Modification of the pGAL14 Yeast Expression Vector pGAL14 is a yeast centromeric expression vector that contains the GAL promoter ($P_{GAL}$), which is induced by the presence of galactose in the medium, and the TRP1 gene. A linker containing a loxP site was generated by annealing together the oligonucleotides listed in SEQ ID NOS:8 and 9. When annealed, these two oligonucleotides form a double-stranded linker having a 5' end compatible with a XhoI sticky end and a 3' end compatible with a NotI sticky end (FIG. 6A). pGAL14 was digested with XhoI and NotI (FIG. 6B) and the annealed loxP linker was inserted to form pGAL14-lox.

EXAMPLE 3

Expression And Purification Of A Gst-Cre Fusion Protein

In order to provide a source of purified Cre recombinase for the in vitro recombination of plasmids, the cre gene was inserted into a Gst expression vector such that a fusion protein comprising Gst at the amino-terminal end and Cre recombinase at the carboxy-terminal end was produced. The Gst-Cre fusion protein was purified by chromatography using Glutathione Sepharose 4B (Pharmacia).

The cre gene was isolated by polymerase chain reaction (PCR) amplification using the plasmid pBS39 (U.S. Pat. No. 4,959,317). U.S. Pat. Nos. 4,683,195, 4,683,202 and 4,965, 188 cover PCR methodology and are incorporated herein by reference. The primers used in the PCR were designed to introduce an NcoI site at the first ATG in the cre open reading frame. The PCR product was cloned into a TA cloning vector (PCRII.1; Invitrogen) and then was subdloned as an NcoI-EcoRI fragment into pGEX-2TKcs (Ex. 2) to generate pQL123. The ligation products were used to transform DH5α cells and the desired recombinant was isolated and used to transform BL21(DE3) cells (Invitrogen).

The nucleotide sequence of the Gst-Cre coding region within pQL123 is listed in SEQ ID NO:10. The amino acid sequence of the fusion protein expressed by pQL123 is listed in SEQ ID NO:11.

To express the Gst-Cre fusion protein, BL21(DE3) cells containing the pQL123 plasmid were grown at 37° C. in LB containing 100 μg/ml ampicillin until the $OD_{600}$ reached 0.6. Expression of the fusion protein was then induced by the addition of IPTG to a final concentration of 0.4 mM and the cells were allowed to grow overnight at 25° C. Following induction, the bacterial cells were pelleted by centrifugation at 5,000×g at 4° C. and the supernatant was discarded. A cell lysate was prepared as follows. Cells harvested from 0.5 liter of culture were suspended in 35 ml of a solution containing 20 mM Tris-HCl, pH 8.0, 0.1M NaCl, 1 mM EDTA, 0.5% Nonidet P-40, 5 μg/ml of each of leupeptin, antipain, aprotinin and 1 mM PMSF at 4° C. The cells were incubated for 10 min on ice and then disrupted by sonication (3×15 sec bursts) using a sonicator (Ultrasonic Heat Systems Model 200R) at full power. The lysate was then clarified by centrifugation at 12,000 rpm using a SS34 rotor (Sorvall).

The Gst-Cre fusion protein was affinity purified from the cell lysate by chromatography on Glutathione Sepharose 4B (Pharmacia) according to the manufacturer's instructions. The protein concentration of Gst-Cre was determined by Bradford analysis (BioRad).

Figure 7:
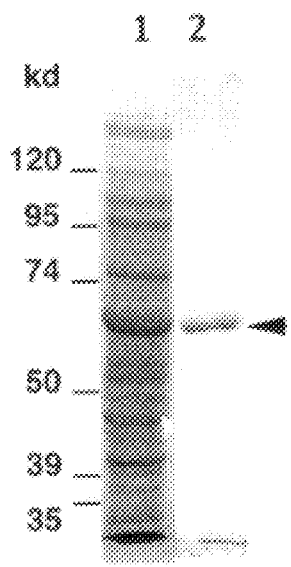
FIG. 7 shows a Coomassie blue-stained SDS-PAGE gel showing the purification of Gst-Cre from *E. coli* cells containing pQL123.

Aliquots of the cell lysate before and after chromatography on Glutathione Sepharose 4B were applied to an SDS-PAGE gel. Following electrophoresis, the gel was stained with Coomassie blue. The stained gel is shown in FIG. 7. In FIG. 7, lanes 1 and 2 contain the cell lysate before and after chromatography, respectively. The arrowhead indicates the Gst-Cre fusion protein. The migration of the molecular weight protein markers is indicated to the left of lane 1. The results shown in FIG. 7 demonstrate the purification of the Gst-Cre fusion protein. This fusion protein was shown to be functional (i.e., capable of mediating recombination between lox sites) in the in vitro recombination assay described below.

EXAMPLE 4

In Vitro Recombination Using The Univector Plasmid Fusion System

The Univector Plasmid Fusion System permits the in vitro recombination of two plasmids. FIG. 8 provides a schematic showing the strategy employed for in vitro recombination. pA represents a generic pUNI vector which contains a loxP site, a kanamycin resistance gene and the conditional R6K origin that is only functional in *E. coli* strains expressing the ΠΙΙ protein (e.g., *E. coli* strains BW18815, BW19094, BW20978, BW20979, BW21037, BW21038). pB represents a generic pHOST vector which contains a loxP site, an ampicillin resistance gene and a Col El origin of replication. pAB represents the fused plasmid which results from the Cre-mediated fusion of pA and pB.

To illustrate the in vitro recombination reaction, pUNI-5 (a pUNI vector which differs from pUNI-10 only in that pUNI-5 retains the NcoI site in the Kn® gene and -contains a different polylinker) was employed as pA and pQL 103, an ampicillin-resistant plasmid containing a loxP site and the ColEl origin, was employed as pB. In a total reaction volume of 20 μl, 0.2 μg of each pUNI-5 (pA) and pQL103 (pB) were mixed in a buffer containing 50 mM Tris-HCl (pH 7.5), 10 mM MgCl₂, 30 mM NaCl and 1 mg/ml BSA. The amount of purified Gst-Cre (Ex. 3) was varied from 0 to 1.0 μg. The reactions were incubated at 37° C. for 20 minutes and then the reactions were placed at 70° C. for 5 min. to inactivate the Gst-Cre protein. Five microliters of each reaction mixture were used directly to transform competent DH5α cells (CaCl₂ treated). The transformed cells were plated onto LB/Amp (100 μg/ml amp) and LB/Kan (40 μg/ml kan) plates and the number of ampicillin resistant (Ap®) and kanamycin-resistant (Kn®) colonies were counted. The results are summarized in Table 1.

TABLE 1

| Gst-Cre (μg/reaction) | Ap$^R$ Colonies | Kn$^R$ Colonies | % of Total Kn$^R$/Ap$^R$ |
| --- | --- | --- | --- |
| 0 | 2.6 × 10$^4$ | 0 | 0 |
| 0.01 | 1.9 × 10$^4$ | 571 | 3 |
| 0.05 | 1.1 × 10$^4$ | 682 | 6.2 |
| 0.1 | 1.5 × 10$^4$ | 502 | 3.3 |
| 0.5 | 0.3 × 10$^4$ | 104 | 3.4 |
| 1.0 | 0.3 × 10$^4$ | 52 | 1.7 |

The results shown in Table 1 demonstrate, that under these reaction conditions 0.05 μg purified Gst-Cre per 20 μl reaction yields the most efficient rate of plasmid fusion. Plasmid DNA was isolated from individual kanamycin-resistant colonies (using standard mini-prep plasmid DNA isolation protocols) and subjected to restriction enzyme digestion to determine the structure of the fused plasmids. This analysis revealed that plasmid DNA isolated from the kanamycin-resistant colonies represented a dimer created by the desired fusion of pUNI-5 and pQL103 via the loxP sites. These results demonstrate that the Univector Plasmid Fusion System can be used to rapidly fuse two plasmids together in vitro.

EXAMPLE 5

In Vitro Fusion Between A pUNI Vector Containing A Gene Of Interest And A Lox-Containing Expression Vector Produces A Fused Vector Capable Of Expressing The Gene Of Interest In Example 4 it was demonstrated that the Univector Plasmid Fusion System can be used to rapidly fuse two plasmid constructs together in vitro. In this example, the ability of the Univector Plasmid Fusion System to fuse two plasmids together in a manner that places the gene of interest contained on the pUNI vector under the transcriptional control of a promoter contained on the pHOST or expression vector in such a manner that a functional protein of interest is expressed from the fused construct.

a) Insertion Of A Gene Of Interest Into The pUNI-10 Vector

The cDNA encoding the wild-type yeast Skpl protein [Bai et al. (1996) Cell 86:263] was cloned into the pUNI-10 vector between the NdeI and BamHI sites to generate pUNI-Skpl; the yeast SKP] cDNA sequence is available as GenBank accession no. U61764. Skpl is an essential protein involved in the regulation of the cell cycle in yeast. Yeast cells containing a temperature sensitive mutant of Skpl cannot grow at the non-permissive temperature (37° C.).

b) In Vitro Fusion Reactions And Complementation Assays pUNI-Skpl was recombined with pGAP24-lox (Ex. 2) and pGAL14-lox (Ex. 2) using the in vitro reaction described in Ex. 4; 0.2 μg of Gst-Cre was used per 20 μl reaction. The resulting plasmid fusions were termed pGAP24-Skpl and pGAL14-Skpl. pGAP24-Skpl and pGAL14-Skpl were then transformed into the temperature sensitive (ts) skpl-11 mutant yeast strain Y555 (Bai et al, supra) and the transformed yeast cells were plated onto SC-tryptophan plates (to select for the expression of the selectable marker TRPl) and incubated at either a permissive (25° C.) or non-permissive temperature (37° C.); the plates which received yeast cells transformed with pGAL14-Skpl contained galactose. The ability of the transformed cells to grow at the non-permissive temperature is dependent upon the expression of the wild-type skpl gene encoded by a properly fused pUNI-Skpl/expression vector construct. As a control, the yeast SKPl genomic clone contained in a URA CEN vector (produced by conventional cloning techniques) was used to transform the ts skpl-11 mutant yeast strain Y555 and the transformed cells were also plated at 25° C. and 37° C. In each case, an expression vector (e.g., pRS414 or pRS415; Bai et al., supra) lacking the SKPl gene but containing the same selectable marker (ie., TRPl) as either pGAP24-Skpl, pGAL14-Skpl or URA CEN-Skpl was used to transform Y555 cells as a control capable of permitting the growth of transformed Y555 cells on selective medium at the permissive temperature.

Figure 9B:
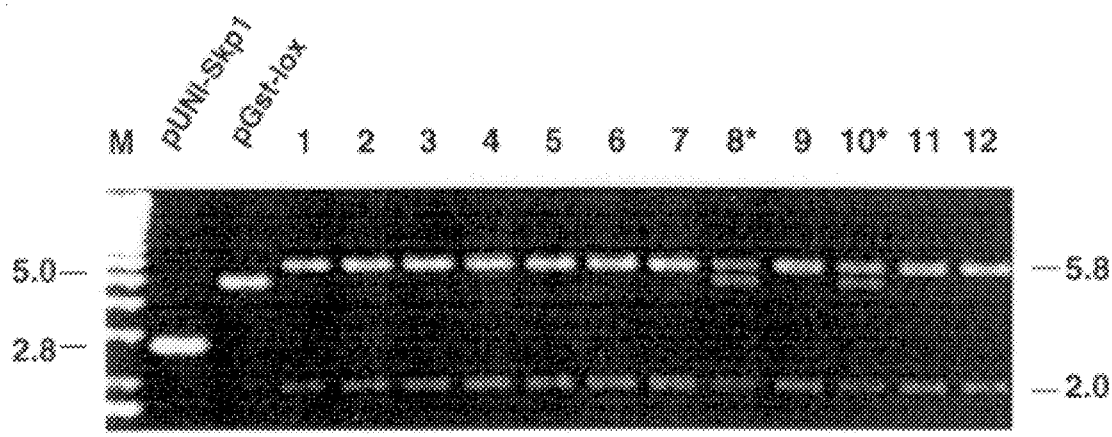
FIG. 9B shows an ethidium bromide-stained gel is showing the separation of restriction fragments generated by the digestion of pUNI-Skp1, pgst-lox and pGst-Skp1.

The results demonstrated that the URA CEN-SKPl construct produced by conventional cloning techniques produced a functional Skpl protein which was capable of complementing the lethality of the SKPl-11 ts mutation. More importantly, the results demonstrated that the in vitro fusion reaction that created pGAP24-Skpl and pGAL14-Skpl produced constructs capable of producing functional Skpl; that is, Y555 cells transformed with either pGAP24-Skpl or pGAL14-Skpl were capable of growth at 37° C., a temperature at which the ts Skpl-11 protein produced by the host strain is non-functional. Expression vectors lacking the SKPl cDNA were incapable of complementing the lethality of the skpl-11 ts mutation.

c) Restriction Analysis, SDS-PAGE Analysis and Western Blot Analysis of In Vitro Fusion Reactions pUNl-Skpl was recombined with pGst-lox (Ex. 2) using the in vitro reaction described in Ex. 4; 0.2 µg of Gst-Cre was used per 20 µl reaction. The resulting plasmid fusion was termed pGST-Skpl. FIG. 9A provides a schematic showing the starting constructs and the predicted fusion construct. Five microliters of the fusion reaction mixture was used transform DH5α cells as described in Ex. 4. The transformed cells were plated onto LB/Amp/Kan plates and plasmid DNA was isolated from individual Ap®Kn® colonies. The plasmid DNAs were digested with PstI followed by electrophoresis on agarose gels to examine the structure of the fused plasmids. A representative ethidium bromide-stained gel is shown in FIG. 9B. In FIG. 9B, lane "M" contains DNA size markers, lanes pUNI-Skpl and pgst-lox contain the starting plasmids digested with PstI and lanes 1–12 contain plasmid DNA from individual AP®Kn® colonies digested with PstI. Lanes marked with an "*" indicate that these colonies contained a trimeric fusion plasmid that resulted from the fusion of two Gst-lox plasmids and one pUNI-Skpl plasmid. The sizes of the two PstI fragments which result from the fusion of pUNI-Skpl and pgst-lox in kb are indicated (5.8 and 2.0 kb). The results shown in FIG. 9B demonstrate that the in vitro fusion reaction resulted in the production of the desired fused construct with high efficiency (about 83% of the plasmids in the AP®Kn® colonies comprised the fusion of one pUNI-Skpl vector with one pgst-lox vector).

Three individual Ap®Kn® colonies were picked and grown in liquid cultures which were induced with IPTG to examine whether the fused construct (pGst-Skpl) could produce the desired Gst-Skpl fusion protein. The cultures were grown, induced and cell extracts were prepared as described in Ex. 6. An aliquot of the cell lysates prepared from induced and uninduced cells were electrophoresed on an SDS-PAGE gel and the gel was either stained with Coomaise blue or transferred to nitrocellulose to generate a Western blot. The Western blot was probed using an anti-Skpl polyclonal antibody (the antibody was raised against the yeast Skpl using conventional methods). The resulting Coomassie-stained gel and Western blot are shown in FIGS. 10A and 10B, respectively.

Figure 10A:
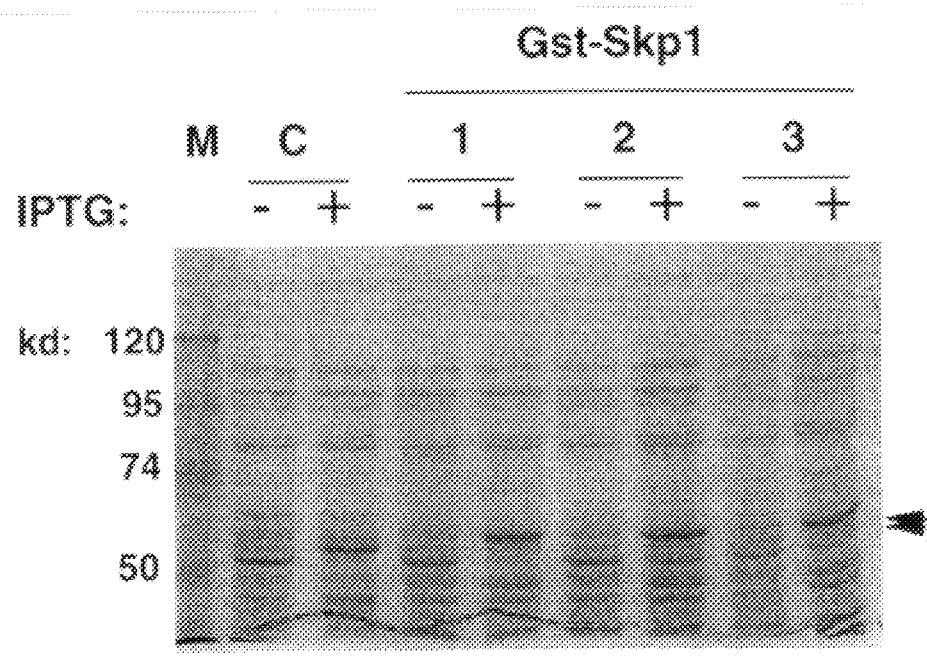
FIG. 10A shows a Coomassie blue-stained SDS-PAGE gel showing the expression of the Gst-Skp1 protein from *E. coli* cells containing pGst-Skp1.

In FIG. 10A, lane "M" contains protein molecular weight markers (size in kd is indicated). Lanes marked "C" contain extracts prepared from E. coli containing a GST-SKPl construct made by conventional cloning [i.e., the SKPl cDNA was excised using restriction enzymes and inserted into pGEX-2TKcs (Ex. 2)]. Lanes 1–3 contain extracts from AP®Kn® cells transformed with in vitro fusion reaction mixtures. Extracts prepared from uninduced cells and IPTG induced cells are indicated by "–" and "+", respectively. The arrowheads indicate the location of the Gst-Skpl fusion proteins; the Gst-Skpl fusion product generated from the pGST-SKPl fusion construct contains 15 additional amino acids which are located between the Gst domain and the Skpl protein sequences relative to the Gst-Skpl fusion protein expressed from the conventionally constructed GST-SKPl plasmid (the additional 15 amino acids are encoded by the linker comprising the loxP site; see FIG. 3). In FIG. 10B, the lane designations are the same as described for FIG. 10A. This Western blot confirms that the bands indicated by the arrowheads in FIG. 10A represent Gst-Skpl fusion proteins.

Figure 10B:
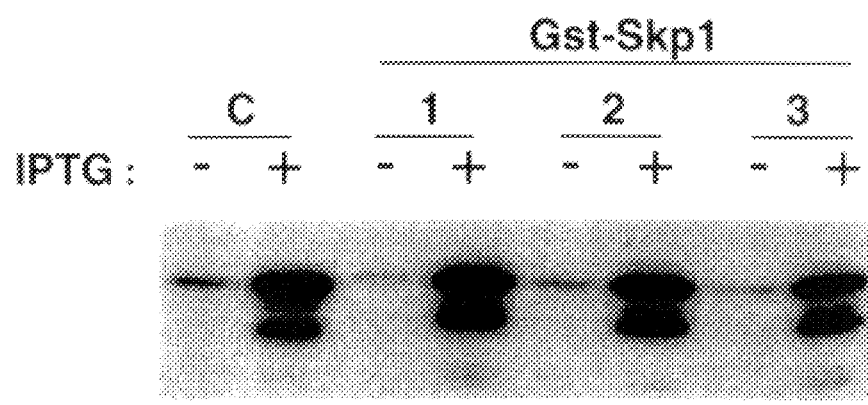
FIG. 10B shows a Western blot of an SDS-PAGE gel containing extracts prepared from *E. coli* cells containing pGst-Skp1 which was probed using an anti-Skp1 antibody.

The results shown in FIGS. 10A and 10B demonstrate that the Univector Fusion System can be used to create an expression vector which maintains the proper translational reading frame and permits the expression of a fusion protein comprising the expression vector-encoded affinity tag and the protein of interest.

The above results demonstrate that the Univector Fusion System can be used to recombine two plasmids, one containing a gene of interest but no promoter (this vector may optionally contain expression signals such as termination signals and/or polyadenylation signals) and the other containing a promoter and optionally other expression signals (e.g., splicing signals, translation initiation codons) (and optionally sequences encoding an affinity domain) but lacking a gene of interest, in vitro in such a manner that the proper translational reading frame is maintained permitting the expression of a functional protein from the fused plasmids in the host cell.

EXAMPLE 6

Construction Of An E. coli Strain That Inducibly Expresses Cre Recombinase

An E. coli strain containing a cre gene under the control of an inducible promoter, termed the QLB4 strain, was constructed as follows. The cre gene was placed under the transcriptional control of the inducible lac promoter by inserting the cre ORF into a derivative of pNN402 [Elledge et al. (1991) Proc. Natl. Acad. Sci. USA 88:1731]; pNN402 was modified to contain a lac promoter. This construct was then crossed onto lambda phage (e.g., λgt11) using conventional techniques. The recombinant lambda phage carrying the lac-cre gene was integrated into the chromosome of E. coli strain JM107 to generate the QLB4 strain.

Figure 11:
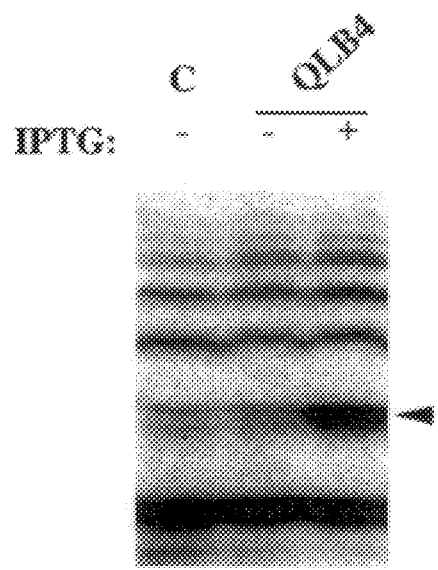
FIG. 11 shows a Western blot of an SDS-PAGE gel containing extracts prepared from *E. coli* cells (QLB4) containing either a conventionally constructed Gst- Skp1 plasmid or pGst-Skp1 (produced by an in vitro fusion reaction).

Expression of Cre recombinase was induced by growing QLB4 cells at 37° C. until an $OD_{600}$ of 0.6 was reached. The culture was then split into 2 parts and IPTG was added to one part to a final concentration of 0.4 mM. As a control, the BNN132 strain (ATCC 47059; Elledge et al. (1991), supra) which contains the cre gene under the transcriptional control of the endogenous cre promoter was treated as described for the QLB4 strain. Cell extracts (total protein) were prepared from all four samples (QLB4±IPTG and BNN132±IPTG) and examined for expression of Cre recombinase by Western blotting analysis. The Western blot was probed using a rabbit polyclonal anti-Cre antibody (Novagen) as the primary antibody and a goat anti-rabbit IgG horseradish peroxidase conjugate (Amershamn) as the secondary antibody according to the manufacturer's instructions. FIG. 11 shows a Western blot containing extracts prepared from (shown left to right) BNN123 cells grown in the absence of IPTG ("C") and QLB4 cells grown in the absence ("QLB4−") and presence of IPTG ("QLB4+"), respectively. The location of the Cre recombinase band is indicated by the arrowhead. The additional bands seen on this Wesrtern blot are due to cross-reactivity of the crude (i.e., not affinity purified) rabbit anti-Cre antibody with bacterial proteins.

Western blot analysis demonstrated that Cre protein could not be detected in BNN123 cells grown in the presence or absence of IPTG. Cre protein was detected in QLB4 cells grown in the presence of IPTG, but not in the absence of IPTG, by Western blot analysis. Therefore, the expression of Cre recombinase in QLB4 cells is greatly induced by the presence of IPTG in the growth medium. By this analysis, the expression of Cre recombinase in QLB4 cells is dependent upon the induction of the lac-cre gene by IPTG. However, more sensitive functional assays indicate that the Cre protein is expressed constitutively at very low levels in both BNN132 cells and QLB4 cells in the absence of IPTG. In these functional assays, a pUNI vector (Kn®) and a pHOST vector (Ap®) were cotransformed into QLB4 cells and the transformed cells were grown on plates containing kanamycin to select for the presence of the pUNI-pHOST fusion plasmid. Plasmid DNA was isolated from individual kanamycin-resistant colonies and subjected to restriction enzyme digestion to examine the structure of the plasmid DNA. This analysis revealed that multiple isoforms of the plasmid fusion product were present in the plasmid DNA isolated from any single kanamycin-resistant colony. While not limiting the present invention to any particular mechanism, it is believed that low level constitutive expression of Cre recombinase leads to multiple fusion events between the pUNI and pHOST vectors resulting in the production of multimeric forms (ie., trimer, tetramer, etc.) of the fused plasmid (the desired fused plasmid is a dimer formed by fusion of pUNI and pHOST). The multimeric plasmid fusion products would be expected to be unstable due to the fact that the Cre protein is constitutively expressed in QLB4 cells.

To overcome the potential problems that low level constitutive expression of the cre gene in the host cell may cause, the expression of cre can be more tightly controlled as described below. In addition the approaches described below, the pUNI and pHOST vectors can be modified as described in Example 7 and these modified vectors can be fused using a host cell that constitutively expresses the Cre protein.

The expression of Cre recombinase can be more tightly controlled by a variety of means. For example, the expression of the cre gene can be made conditional when expressing cre under the control of the lac promoter by growing the host cells in medium containing glucose. The presence of 0.2% glucose in the growth medium virtually shuts down transcription form the lac promoter. In addition, the lac promoter can be modified to insert additional operator (o) sites which bind the lac repressor. Other tightly controlled promoters are known to the art [e.g., the T7 promoter which requires the expression of T7 RNA polymerase; these promoters are available on the pET vectors (Novagen)] and may be employed to control the expression of the cre gene.

In addition to placing the cre ORF under the control of a tightly controlled promoter, Cre expression can be tightly controlled by placing the cre gene on a plasmid containing a temperature-sensitive (ts) replicon (e.g., rep pSC101$^{ts}$). When the cre gene is carried on a ts replication plasmid, Cre will be expressed during the transformation of the host cell (because the host cell containing the ts plasmid containing the cre gene was maintained at the permissive temperature) but will be absent following recombination of the pUNI and pHOST vectors when the host cell is grown at a temperature non-permissive for replication of the ts replicon.

EXAMPLE 7

In Vivo Recombination In Procaryotic Hosts Using The Univector Fusion System

As described in Example 6, cotransformation of E. coli cells expressing Cre protein (e.g., QLB4, BNN132) with a pUNI construct and a pHOST construct (each construct containing a single lox site) results in the fusion of these two constructs in vivo. If the host cell used for the recombination reaction constitutively expresses the Cre protein, multimeric forms of the fused constructs are generated. In addition to the methods outlined above for tightly regulating the expression of the cre gene in the host cell, cells constitutively producing Cre protein can be employed with modified pUNI and pHOST vectors as described in this example. The pUM construct is modified such that two different lox sites flank the kanamycin resistance gene (the modified pUNI construct is termed pUNI-D). The two lox sites differ in their spacer regions by one or two nucleotides and for the sake of discussion the two different lox sites are referred to as "loxA" and "loxB" (e.g., loxP and loxP511; "loxb" is used in this discussion to distinguish it from the first lox site termed "loxA" and does not indicate the use of the loxB sequence found in the E. coli chromosome). Cre cannot efficiently catalyze a recombination event between a loxA site and a loxb due to the sequence changes located in the spacer regions between the Cre binding sites; however Cre can efficiently catalyze the recombination between two loxA sites or two loxB sites [Hoess et al. (1986) Nucleic Acids Res.14:2287]. The pHOST construct is modified such that one loxA site and one loxB site flank the selectable marker gene (the modified pHOST construct is termed pHOST-D). In this example, pHOST contains the sacB gene as the selectable marker (a negative selectable marker). The presence of the sacB gene on pHOST-D provides a means of counter-selection as cells expressing the sacB gene are killed when the cell is grown in medium containing 5% sucrose [Gay et al. (1985) J. Bacteriol. 164:918 and (1983) J. Bacteriol. 153:1424].

FIG. 12 provides a schematic showing the strategy for in vivo recombination in a Cre-expressing host cell (e.g., QLB4 cells) using the pUNI-D and pHOST-D constructs. Arrows are used to indicate the direction of transcription of various genes or gene segments in FIG. 12. In FIG. 12, the following abbreviations are used: Ap® (ampicillin resistance gene); Kn® (kanamycin resistance gene); Ori (non-conditional plasmid origin of replication); Ori® (the R6Kγ conditional origin of replication); Cre (Cre recombinase); GENEX (gene of interest). The strategy outlined in FIG. 12 is referred to as the "in vivo gene-trap". FIG. 12 illustrates that the second lox site (loxB) in pUNI-D (relative to the design of the pUNI-10 vector) is inserted between the kanamycin resistance gene and the R6Kγ conditional origin of replication.

To generate a pHOST-D construct, a commercially available expression vector containing the desired promoter (and optionally enhancer) is modified as described in Ex. 2 to insert the loxA site downstream of the promoter (it is not necessary that a commercially available expression vector be employed as the art is well aware of methods for the generation of expression vectors). Sequences encoding the sacB gene [Gay et al. (1983) J. Bacteriol. 153:1424; GenBank accession nos. X02730 and K01987] and the second lox site (loxB) are inserted downstream of the first lox site (loxA).

The pUNI-D and pHOST-D constructs are cotransformed into QLB4 cells (Ex. 6) and the transformed cells are plated onto LB/Ap/Kn plates containing 5% sucrose to select for the desired recombinant. FIG. 12 illustrates the recombination events which will occur in the presence of Cre in the QLB4 cells. First pUNI-D and pHOST-D will fuse to form two dimers in which two possible double cross-over events can occur. These two double cross-over events are diagrammed in FIG. 12. The double cross-over events will result in the exchange of the DNA segments that are flanked by loxA and loxB to produce the plasmids labelled "A" and "B." All plamsids which contain the sacB gene (the pHOST-D, the fused plasmids and plasmid B) will be selected against by the presence of sucrose in the growth medium. The pUNI-D construct will not be able to replicate in QLB4 cells as these cells do not express the II protein required for replication of the R6Kγ origin. Therefore, the only construct will be maintained in QLB4 cells selected on LB/Kn containing sucrose is the desired plasmid A in which the gene of interest from pUNI-D has been placed under the transcriptional control of the promoter located on pHOST-D.

pUNI-10 was modified to place a second lox site, comprising the loxP511 sequence (SEQ ID NO:16) between the kanamycin resistance gene and the R6Kγ conditional origin of replication to create pUNI-10-D. A second lox site, comprising the loxP511 site, was inserted onto a loxP-containing expression plasmid (i.e., a pHOST vector) to create a pHOST-D vector. One-half of one microgram of each plasmid was cotransformed into competent QLB4 cells and an aliquot of the transformed cells were plated onto LB/Ap plates and onto LB/Ap/Kn plates containing 5% sucrose and the number of colonies on each type of plate were counted. The percentage of AP®Kn® colonies which grew on sucrose-containing plates relative to the number of Ap® colonies was 1% ($1\times10^3/1\times10^5$). Restriction enzyme digestion of plasmid DNA isolated from individual Ap®KW® colonies which grew on sucrose-containing plates confirmed that the desired fusions had been generated. These results indicate that the in vivo gene trap method can be used to recombine a gene of interest carried on a pUNI-D vector into an expression vector using host cells that constiutively express the Cre protein.

In addition to providing a means for recombining a gene of interest carried on a pUNI-D vector into an expression vector using host cells that constitutively express the Cre protein, the in vivo gene trap method provides a means to transfer a gene of interest contained on a linear DNA molecule (e.g., a PCR product) that lacks a selectable marker into an expression vector(s). The desired PCR product is amplified using two primers, each of which encode a different lox site (a "loxA" and "loxB" site such as a loxP and loxP511 site). A pUNI vector is constructed that contains (5' to 3') a loxA site, a counter-selectable marker such as the sacB gene and a lox B site (i.e., the two different lox sites flank the counter-selectable marker). This pUNI vector also contains a conditional origin of replication and an antibiotic resistance gene as described above and in Ex. 1. The PCR product (loxA-amplified sequence-loxB) is recombined with the modified pUNI vector (which comprises loxA-counter-selectable marker-loxB) to create a pUNI vector containing the PCR product which now lacks the counter-selectable marker; this recombination event is selected for by growing the host cells in medium which kills the host if the counter-selectable gene is expressed. The PCR product in the pUNI vector (containing 2 lox sites) can then be placed under the control of the desired promoter element by recombining the pUNI/PCR product construct with the appropriate pHOST-D vector.

EXAMPLE 8

The Use Of Modified LoxP Sites To Increase Expression Of The Protein Of Interest The pUNI and pHOST constructs employed in the Univector Plasmid Fusion System were designed such that plasmid fusion results in the introduction of a lox site between the promoter and the gene of interest. LoxP sites consist of two 13 bp inverted repeats separated by an 8 bp spacer region [Hoess et al. (1982) Proc. Natl. Acad. Sci. USA 79:3398 and U.S. Pat. No. 4,959,317]. Transcripts of the gene of interest produced from a pUNI-pHOST fusion construct comprising a loxP site may have two 13 nucleotide perfect inverted repeats within the 5' untranslated region (UTR) which have the potential to form a stem-loop structure (this will occur in those cases where pHOST does not encode an affinity domain at the amnino-terminus of the fusion protein). It is currently believed that the ribosome scanning mechanism is the most commonly used mechanism for initiation of translation in eukaryotes (e.g., yeast and mammalian cells). Using this mechanism, the ribosome binds to the 5' cap structure of the mRNA transcript and scans downstream along the 5' UTR searching for the first ATG or translation start codon. Without limiting the present invention to any particular mechanism, it is possible that a stem-loop structure formed by the presence of a loxP sequence on the 5' UTR of the mRNA encoding the protein of interest would block or reduce the efficiency ribosome scanning and thus the translation initiation step could be impaired. There is evidence that stem-loop structures in the 5' UTR of particular mRNAs reduce the efficiency of translation in eukaryotes [see, e.g., Donahue et al. (1988) Mol. Cell. Biol. 8:2964 and Yoon et al. Genes and Dev. (1992) 6:2463]. It is noted that no evidence suggests that the presence of a stem-loop structure in the coding region (as opposed to the 5' UTR) of a transcript negatively affects its ability to be translated. It is likely that the energy of protein synthesis is sufficient to overcome secondary structures present in mRNAs. Indeed the data presented in Ex. 5 shows that a GST-SKP1 fusion construct produced using the Univector Fusion System (i.e., the construct contains a loxP site between the sequences encoding the Gst and Skpl domains) produced the same level of fusion protein as did a conventional construct encoding a Gst-Skp1 fusion protein which lacks the loxP sequence. Therefore, concerns over the presence of a stem-loop structure caused by the presence of a lox sequence in a transcript encoded by a pUNI-pHOST fusion construct are limited to those constructs which do not generate fusion proteins.

If low levels of expression are observed when a gene of interest is expressed from a pUNI-pHOST fusion constructs comprising lox sequences that comprise perfect 13 bp inverted repeats (e.g., loxP), pUNI and pHOST constructs containing mutated loxP sequences are employed. The mutated loxP sequences comprise point mutations that create mismatches between the two 13 bp inverted repeat sequences within the loxP site which disrupt the formation of or reduce the stability of a stem loop structure. Specifically, two modified loxP sites were designed that have mismatches at different positions in the inverted repeats located within a loxP site. The 13 bp inverted repeats are binding sites for the Cre protein; thus, each loxP site has two binding sites for Cre. For the purpose of discussion, these two binding sites are referred to as L and R (left and right). The wild-type loxP site is designed L(0)-R(0) wherein "0" indicates the absence of a mutation (ie., the wild-type sequence). Two derivatives of the wild-type loxP sequence were designed and termed loxP2 and loxP3. The sequence of loxP2 (SEQ ID NO:13), loxP3 (SEQ ID NO:14), as well as the wild-type loxP sequence (SEQ ID NO:12) are shown in FIG. 13. LoxP2 is placed on the pUNI-10 construct (in place of the wild-type loxP site) and loxP3 is placed on the pHOST construct.

LoxP2 has repeats designated L(3,6)-R(0) which indicates that the third and sixth nucleotides of the left repeat are mutated; thus, a mismatch is introduced at the third and sixth positions between the L and R repeats of the loxP2 site. LoxP3 has repeats designated L(0)-R(9) which indicates that the ninth nucleotide on the right repeat sequence is mutated to introduce a mismatch at the ninth position between the L and R repeats of the loxP3 site. Fusion between the loxP2 site on the pUNI construct and the loxP3 site on the pHOST construct will generate a hybrid loxP23 site [L(3,6)-R (9)] located between the promoter and the gene of interest and a wild-type loxP site [L(0)-R(0)] at the distal junction. Thus, the loxP23 site (SEQ ID NO:15) in the 5' UTR will have three mismatches distributed at positions 3, 6 and 9 between the 13 nucleotide inverted repeats which are expected to strongly destabilize the formation of the stem-loop structure. Other mutated loxP sequences suitable for disruption of the stem-loop structure will be apparent to those skilled in the art; therefore, the present invention is not limited to the use of the loxP2 and loxP3 sequences for the purpose of disrupting stem-loop formation on the 5' UTR of transcripts produced from pUNI-pHOST fusion constructs. The suitability of any pair of mutated lox sites for use in the Univector Fusion system may be tested by placing one member of the pair on a pUNI vector and the other member on a pHOST construct. The two modified vectors are then recombined in vitro as described in Ex. 4 and the fusion reaction mixture is used to transform E. coli cells and the transformed cells are plated on selective medium (e.g., on LB/Amp and LB/Kan plates) in order to determine the efficiency of recombination between the two mutated lox sites (Ex. 4). The efficiency of recombination between the two mutated lox sites is compared to the efficiency of recombination between two wild-type lox sites. Any pair of two different mutant lox sites that recombines at a rate that is about 5% or greater than that observed using two loxP sites is a useful pair of mutated lox sites for use in avoiding the formation of a stem-loop structure on the 5' UTR of the mRNA transcribed from the pUNI/pHOST fusion construct.

It will be apparent to those skilled in the art that a similar strategy can be employed for the modification of frt sites when the FLP recombinase is employed for the recombination event. The frt site, like lox sites, contains two 13 bp inverted repeats separated by an 8 bp spacer region.

It is clear from the above that the present invention provides methods for the subcloning of nucleic acid molecules that permit the rapid transfer of a target nucleic acid sequence (e.g., a gene of interest) from nucleic acid molecule to another in vitro or in vivo without the need to rely upon restriction enzyme digestions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A pUNI vector construct comprising, in 5' to 3' operable order:
   a) a conditional origin of replication;
   b) a sequence-specific recombinase target site having a 5' and a 3' end; and
   c) a unique restriction enzyme site, said restriction enzyme site located adjacent to said 3' end of said sequence-specific recombinase target site.

2. The vector construct of claim 1 further comprising a prokaryotic termination sequence located 3' to said unique restriction enzyme site.

3. The vector construct of claim 2, wherein said prokaryotic termination sequence is the T7 termination sequence.

4. The vector construct of claim 1 further comprising a eukaryotic polyadenylation sequence located 3' and adjacent to said unique restriction enzyme site.

5. The vector construct of claim 4, wherein said polyadenylation sequence is selected from the group consisting of the bovine growth hormone polyadenylation sequence, the simian virus 40 polyadenylation sequence and the Herpes simplex virus thymidine kinase polyadenylation sequence.

6. The vector construct of claim 1 further comprising a selectable marker gene.

7. The vector construct of claim 6, wherein said selectable marker is selected from the group consisting of kanamycin resistance gene, the ampicillin resistance gene, the tetracycline resistance gene, the chloramphenicol resistance gene, the streptomycin resistance gene, the strA gene and the sacB gene.

8. The vector construct of claim 1, wherein said sequence-specific recombinase target site is selected from the group consisting of loxP, loxP2, loxP3, loxP23, loxP511, loxB, loxC2, loxL, loxR, loxΔ86, loxΔ117, frt, dif, and att.

9. The vector construct of claim 1 further comprising a gene of interest inserted into said unique restriction enzyme site.

10. The vector construct of claim 1, wherein said vector construct is pUNI-10, comprising the nucleotide sequence set forth in SEQ ID NO:1.

11. A pUNI vector construct comprising, in 5' to 3' operable order:
   a) a conditional origin of replication;
   b) a sequence-specific recombinase target site; and
   c) a polylinker, said polylinker located adjacent to said 3' end of said sequence-specific recombinase target site.

12. A pHOST expression vector construct comprising in 5' to 3' operable order:
   a) an origin of replication;
   b) a promoter element; and
   c) a sequence-specific recombinase target site.

13. The expression vector construct of claim 12 further comprising a selectable marker gene.

14. A fused expression vector construct produced by the recombination of a pUNI vector and a pHOST expression vector, said fused expression vector comprising in 5' to 3' operable order:
   a) a promoter element;
   b) a first sequence-specific recombinase target site having a 5' and a 3' end;
   c) a gene of interest joined to said 3' end of said sequence-specific recombinase target site such that a functional translational reading frame is created;
   d) a conditional origin of replication;
   e) a first selectable marker gene;
   f) a second sequence-specific recombinase target site; and
   g) an origin of replication.

15. The fused expression vector construct of claim 14 further comprising a second selectable marker gene.

16. A method for the in vitro recombination of a pUNI vector and a pHOST expression vector to form a fused expression vector, said method comprising:

a) providing:
  i) a pUNI vector construct comprising, in 5' to 3' operable order, a conditional origin of replication, a first sequence-specific recombinase target site and a first selectable marker gene;
  ii) a pHOST expression vector construct comprising, in 5' to 3' operable order, an origin of replication, a promoter element and a second sequence-specific recombinase target site; and
  iii) a site-specific recombinase;
b) contacting said pUNI vector and pHOST expression vector constructs in vitro with said site-specific recombinase under conditions such that said first and second constructs are recombined to form a single fused expression vector.

17. The method of claim 16, wherein said pUNI vector construct further comprises a gene of interest located adjacent to said 3' end of said first sequence-specific recombinase target site and before the selectable marker gene, wherein the recombination of said pUNI vector and pHOST expression vector constructs places said gene of interest under the transcriptional control of said promoter element within said fused expression vector.

18. The method of claim 17, wherein said pHOST expression vector construct further comprises a nucleotide sequence encoding an affinity domain and the recombination of said pUNI vector and pHOST exression vector constructs results in placing said gene of interest in frame with said sequence encoding said affinity domain, thereby encoding a fusion protein having the affinity domain located at either the amino- or carboxy-terminus of said fusion protein.

19. The method of claim 16, wherein said pHOST vector construct further comprises a second selectable marker gene, said second selectable marker being different from said first selectable marker.

20. A method for the recombination of pUNI vector and pHOST expression vector constructs to form a single fused expression vector in a prokaryotic host, comprising:

a) providing:
  i) a pUNI vector construct comprising a conditional origin of replication, a first sequence-specific recombinase target site having a 5' and a 3' end, a unique restriction enzyme site, said restriction enzyme site located adjacent to said 3' end of said sequence-specific recombinase target site, and a first selectable marker gene;
  ii) a pHOST expression vector construct comprising in 5' to 3' operable order, an origin of replication, a promoter element having a 5' and a 3' end and a second sequence-specific recombinase target site having a 5' and a 3' end;
  iii) a prokarvotic host cell expressing a site-specific recombinase;
b) introducing said pUNI vector and pHOST expression vector constructs into said prokaryotic host cell, wherein said host cell expresses a site-specific recombinase, under conditions such that said pUNI vector and pHOST expression vector constructs are recombined to form a single fused expression vector.

21. The method of claim 20 further comprising growing said host cell containing said single fused expression vector under conditions which select for the presence of said single fused expression vector.

22. The method of claim 20, wherein said pUNI vector construct further comprises a prokaryotic termination sequence.

23. The method of claim 20, wherein said pUNI vector construct further comprises a gene of interest inserted into said unique restriction enzyme site.

24. The method of claim 20, wherein said pUNI vector construct further comprises a eukaryotic polyadenylation sequence.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 2220 base pairs
        ( B ) TYPE: nucleic acid
        ( C ) STRANDEDNESS: double
        ( D ) TOPOLOGY: circular ( i i ) MOLECULE TYPE: other nucleic acid
        ( A ) DESCRIPTION: /desc = "DNA"

( x i ) SEQUENCE DESCRIPTION: SEQ ID NO:1:

```
AATTCTGTCA    GCCGTTAAGT    GTTCCTGTGT    CACTGAAAAT    TGCTTTGAGA    GGCTCTAAGG       60

GCTTCTCAGT    GCGTTACATC    CCTGGCTTGT    TGTCCACAAC    CGTTAAACCT    TAAAAGCTTT      120

AAAAGCCTTA    TATATTCTTT    TTTTCTTAT     AAAACTTAAA    ACCTTAGAGG    CTATTTAAGT      180

TGCTGATTTA    TATTAATTTT    ATTGTTCAAA    CATGAGAGCT    TAGTACGTGA    AACATGAGAG      240
```

-continued

| | | | | | |
|---|---|---|---|---|---|
| CTTAGTACGT | TAGCCATGAG | AGCTTAGTAC | GTTAGCCATG | AGGGTTTAGT | TCGTTAAACA | 300
| TGAGAGCTTA | GTACGTTAAA | CATGAGAGCT | TAGTACGTGA | AACATGAGAG | CTTAGTACGT | 360
| ACTATCAACA | GGTTGAACTG | CTGATCAACA | GATCCTCTAC | GCGGCCGCGG | TACCATAACT | 420
| TCGTATAGCA | TACATTATAC | GAAGTTATCT | GGAATTCCCC | GGGCTCGAGA | ACATATGGCC | 480
| ATGGGGATCC | GCGGCCGCAA | TTGTTAACAG | ATCCGTCGAC | GAGCTCGCTA | TCAGCCTCGA | 540
| CTGTGCCTTC | TAGTTGCCAG | CCATCTGTTG | TTTGCCCCTC | CCCCGTGCCT | TCCTTGACCC | 600
| TGGAAGGTGC | CACTCCCACT | GTCCTTTCCT | AATAAAATGA | GGAAATTGCA | TCGCATTGTC | 660
| TGAGTAGGTG | TCATTCTATT | CTGGGGGGTG | GGGTGGGGCA | GGACAGCAAG | GGGGAGGATT | 720
| GGGAAGACAA | TAGCAGGCAT | GCTGGGGATT | CTAGAAGATC | CGGCTGCTAA | CAAAGCCCGA | 780
| AAGGAAGCTG | AGTTGGCTGC | TGCCACCGCT | GAGCAATAAC | TAGCATAACC | CCTTGGGGCC | 840
| TCTAAACGGG | TCTTGAGGGG | TTTTTGCTG  | AAAGGAGGAA | CTATATCCGG | ATATCCCGGG | 900
| GTGGGCGAAG | AACTCCAGCA | TGAGATCCCC | GCGCTGGAGG | ATCATCCAGC | CGGCGTCCCG | 960
| GAAAACGATT | CCGAAGCCCA | ACCTTTCATA | GAAGGCGGCG | GTGGAATCGA | AATCTCGTGA | 1020
| TGGCAGGTTG | GGCGTCGCTT | GGTCGGTCAT | TTCGAACCCC | AGAGTCCCGC | TCAGAAGAAC | 1080
| TCGTCAAGAA | GGCGATAGAA | GGCGATGCGC | TGCGAATCGG | GAGCGGCGAT | ACCGTAAAGC | 1140
| ACGAGGAAGC | GGTCAGCCCA | TTCGCCGCCA | AGCTCTTCAG | CAATATCACG | GGTAGCCAAC | 1200
| GCTATGTCCT | GATAGCGGTC | CGCCACACCC | AGCCGGCCAC | AGTCGATGAA | TCCAGAAAAG | 1260
| CGGCCATTTT | CCACCATGAT | ATTCGGCAAG | CAGGCATCGC | CATGGGTCAC | GACGAGATCC | 1320
| TCGCCGTCGG | GCATGCGCGC | CTTGAGCCTG | GCGAACAGTT | CGGCTGGCGC | GAGCCCCTGA | 1380
| TGCTCTTCGT | CCAGATCATC | CTGATCGACA | AGACCGGCTT | CCATCCGAGT | ACGTGCTCGC | 1440
| TCGATGCGAT | GTTTCGCTTG | GTGGTCGAAT | GGGCAGGTAG | CCGGATCAAG | CGTATGCAGC | 1500
| CGCCGCATTG | CATCAGCCAT | GATGGATACT | TTCTCGGCAG | GAGCAAGGTG | AGATGACAGG | 1560
| AGATCCTGCC | CCGGCACTTC | GCCCAATAGC | AGCCAGTCCC | TTCCCGCTTC | AGTGACAACG | 1620
| TCGAGCACAG | CTGCGCAAGG | AACGCCCGTC | GTGGCCAGCC | ACGATAGCCG | CGCTGCCTCG | 1680
| TCCTGCAGTT | CATTCAGGGC | ACCGGACAGG | TCGGTCTTGA | CAAAAAGAAC | CGGGCGCCCC | 1740
| TGCGCTGACA | GCCGGAACAC | GGCGGCATCA | GAGCAGCCGA | TTGTCTGTTG | TGCCCAGTCA | 1800
| TAGCCGAATA | GCCTCTCCAC | CCAAGCGGCC | GGAGAACCTG | CGTGCAATCC | ATCTTGTTCA | 1860
| ATCATGCGAA | ACGATCCTCA | TCCTGTCTCT | TGATCAGATC | TTGATCCCCT | GCGCCATCAG | 1920
| ATCCTTGGCG | GCAAGAAAGC | CATCCAGTTT | ACTTTGCAGG | GCTTCCCAAC | CTTACCAGAG | 1980
| GGCGCCCCAG | CTGGCAATTC | CGGTTCGCTT | GCTGTCCATA | AAACCGCCCA | GTCTAGCTAT | 2040
| CGCCATGTAA | GCCCACTGCA | AGCTACCTGC | TTTCTCTTTG | CGCTTGCGTT | TTCCCTTGTC | 2100
| CAGATAGCCC | AGTAGCTGAC | ATTCATCCGG | GGTCAGCACC | GTTTCTGCGG | ACTGGCTTTC | 2160
| TACGTGTTCC | GCTTCCTTTA | GCAGCCCTTG | CGCCCTGAGT | GCTTGCGGCA | GCGTGAAGCT | 2220

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:2:

GGATCCCCGG GAATTC                                                                                  16

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:3:

GGATCGCATA TGCCCATGGC TCGAGGATCC GAATTC                                                            36

( 2 ) INFORMATION FOR SEQ ID NO:4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:4:

CATGGCTATA ACTTCGTATA GCATACATTA TACGAAGTTA TG                                                     42

( 2 ) INFORMATION FOR SEQ ID NO:5:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:5:

GATCCATAAC TTCGTATAAT GTATGCTATA CGAAGTTATA GC                                                     42

( 2 ) INFORMATION FOR SEQ ID NO:6:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:6:

GGCCGGACGT CATAACTTCG TATAGCATAC ATTATACGAA GTTATG                                                 46

( 2 ) INFORMATION FOR SEQ ID NO:7:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:7:

GATCCATAAC TTCGTATAAT GTATGCTATA CGAAGTTATG ACGTCC 46

( 2 ) INFORMATION FOR SEQ ID NO:8:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:8:

TCGAGACGTC ATAACTTCGT ATAGCATACA TTATACGAAG TTATGC 46

( 2 ) INFORMATION FOR SEQ ID NO:9:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:9:

GGCCGCATAA CTTCGTATAA TGTATGCTAT ACGAAGTTAT GACGTC 46

( 2 ) INFORMATION FOR SEQ ID NO:10:

( i ) SEQUENCE CHARACTERISTICS:
    ( A ) LENGTH: 1740 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc = "DNA"

( i x ) FEATURE:
    ( A ) NAME/KEY: CDS
    ( B ) LOCATION: 1..1737

( x i ) SEQUENCE DESCRIPTION: SEQ ID NO:10:

| ATG | TCC | CCT | ATA | CTA | GGT | TAT | TGG | AAA | ATT | AAG | GGC | CTT | GTG | CAA | CCC | 48 |
| Met | Ser | Pro | Ile | Leu | Gly | Tyr | Trp | Lys | Ile | Lys | Gly | Leu | Val | Gln | Pro | |
| 1 | | | | 5 | | | | | 10 | | | | | 15 | | |

| ACT | CGA | CTT | CTT | TTG | GAA | TAT | CTT | GAA | GAA | AAA | TAT | GAA | GAG | CAT | TTG | 96 |
| Thr | Arg | Leu | Leu | Leu | Glu | Tyr | Leu | Glu | Glu | Lys | Tyr | Glu | Glu | His | Leu | |
| | | | | 20 | | | | | 25 | | | | | 30 | | |

| TAT | GAG | CGC | GAT | GAA | GGT | GAT | AAA | TGG | CGA | AAC | AAA | AAG | TTT | GAA | TTG | 144 |
| Tyr | Glu | Arg | Asp | Glu | Gly | Asp | Lys | Trp | Arg | Asn | Lys | Lys | Phe | Glu | Leu | |
| | | 35 | | | | | 40 | | | | | 45 | | | | |

| GGT | TTG | GAG | TTT | CCC | AAT | CTT | CCT | TAT | TAT | ATT | GAT | GGT | GAT | GTT | AAA | 192 |
| Gly | Leu | Glu | Phe | Pro | Asn | Leu | Pro | Tyr | Tyr | Ile | Asp | Gly | Asp | Val | Lys | |
| | 50 | | | | | 55 | | | | | 60 | | | | | |

| TTA | ACA | CAG | TCT | ATG | GCC | ATC | ATA | CGT | TAT | ATA | GCT | GAC | AAG | CAC | AAC | 240 |
| Leu | Thr | Gln | Ser | Met | Ala | Ile | Ile | Arg | Tyr | Ile | Ala | Asp | Lys | His | Asn | |
| 65 | | | | | 70 | | | | | 75 | | | | | 80 | |

| ATG | TTG | GGT | GGT | TGT | CCA | AAA | GAG | CGT | GCA | GAG | ATT | TCA | ATG | CTT | GAA | 288 |
| Met | Leu | Gly | Gly | Cys | Pro | Lys | Glu | Arg | Ala | Glu | Ile | Ser | Met | Leu | Glu | |
| | | | | 85 | | | | | 90 | | | | | 95 | | |

| GGA | GCG | GTT | TTG | GAT | ATT | AGA | TAC | GGT | GTT | TCG | AGA | ATT | GCA | TAT | AGT | 336 |
| Gly | Ala | Val | Leu | Asp | Ile | Arg | Tyr | Gly | Val | Ser | Arg | Ile | Ala | Tyr | Ser | |
| | | | 100 | | | | | 105 | | | | | 110 | | | |

| | | | | | | | | | | | | | | | |
|---|---|---|---|---|---|---|---|---|---|---|---|---|---|---|---|
| AAA | GAC | TTT | GAA | ACT | CTC | AAA | GTT | GAT | TTT | CTT | AGC | AAG | CTA | CCT | GAA | 384 |
| Lys | Asp | Phe 115 | Glu | Thr | Leu | Lys | Val 120 | Asp | Phe | Leu | Ser | Lys 125 | Leu | Pro | Glu | |
| ATG | CTG | AAA | ATG | TTC | GAA | GAT | CGT | TTA | TGT | CAT | AAA | ACA | TAT | TTA | AAT | 432 |
| Met | Leu 130 | Lys | Met | Phe | Glu | Asp 135 | Arg | Leu | Cys | His | Lys 140 | Thr | Tyr | Leu | Asn | |
| GGT | GAT | CAT | GTA | ACC | CAT | CCT | GAC | TTC | ATG | TTG | TAT | GAC | GCT | CTT | GAT | 480 |
| Gly | Asp | His | Val | Thr | His 150 | Pro | Asp | Phe | Met | Leu 155 | Tyr | Asp | Ala | Leu | Asp 160 | |
| Gly 145 | | | | | | | | | | | | | | | | |
| GTT | GTT | TTA | TAC | ATG | GAC | CCA | ATG | TGC | CTG | GAT | GCG | TTC | CCA | AAA | TTA | 528 |
| Val | Val | Leu | Tyr | Met 165 | Asp | Pro | Met | Cys | Leu 170 | Asp | Ala | Phe | Pro | Lys 175 | Leu | |
| GTT | TGT | TTT | AAA | AAA | CGT | ATT | GAA | GCT | ATC | CCA | CAA | ATT | GAT | AAG | TAC | 576 |
| Val | Cys | Phe | Lys 180 | Lys | Arg | Ile | Glu | Ala 185 | Ile | Pro | Gln | Ile | Asp 190 | Lys | Tyr | |
| TTG | AAA | TCC | AGC | AAG | TAT | ATA | GCA | TGG | CCT | TTG | CAG | GGC | TGG | CAA | GCC | 624 |
| Leu | Lys | Ser 195 | Ser | Lys | Tyr | Ile | Ala 200 | Trp | Pro | Leu | Gln | Gly 205 | Trp | Gln | Ala | |
| ACG | TTT | GGT | GGT | GGC | GAC | CAT | CCT | CCA | AAA | TCG | GAT | CTG | GTT | CCG | CGT | 672 |
| Thr | Phe 210 | Gly | Gly | Gly | Asp | His 215 | Pro | Pro | Lys | Ser | Asp 220 | Leu | Val | Pro | Arg | |
| GGA | TCT | CGT | CGT | GCA | TCT | GTT | GGA | TCG | CAT | ATG | CCC | ATG | GCC | AAT | TTA | 720 |
| Gly 225 | Ser | Arg | Arg | Ala | Ser 230 | Val | Gly | Ser | His | Met 235 | Pro | Met | Ala | Asn | Leu 240 | |
| CTG | ACC | GTA | CAC | CAA | AAT | TTG | CCT | GCA | TTA | CCG | GTC | GAT | GCA | ACG | AGT | 768 |
| Leu | Thr | Val | His | Gln 245 | Asn | Leu | Pro | Ala | Leu 250 | Pro | Val | Asp | Ala | Thr 255 | Ser | |
| GAT | GAG | GTT | CGC | AAG | AAC | CTG | ATG | GAC | ATG | TTC | AGG | GAT | CGC | CAG | GCG | 816 |
| Asp | Glu | Val | Arg 260 | Lys | Asn | Leu | Met | Asp 265 | Met | Phe | Arg | Asp | Arg 270 | Gln | Ala | |
| TTT | TCT | GAG | CAT | ACC | TGG | AAA | ATG | CTT | CTG | TCC | GTT | TGC | CGG | TCG | TGG | 864 |
| Phe | Ser | Glu 275 | His | Thr | Trp | Lys | Met 280 | Leu | Leu | Ser | Val | Cys 285 | Arg | Ser | Trp | |
| GCG | GCA | TGG | TGC | AAG | TTG | AAT | AAC | CGG | AAA | TGG | TTT | CCC | GCA | GAA | CCT | 912 |
| Ala | Ala 290 | Trp | Cys | Lys | Leu | Asn 295 | Asn | Arg | Lys | Trp | Phe 300 | Pro | Ala | Glu | Pro | |
| GAA | GAT | GTT | CGC | GAT | TAT | CTT | CTA | TAT | CTT | CAG | GCG | CGC | GGT | CTG | GCA | 960 |
| Glu | Asp | Val | Arg | Asp 310 | Tyr | Leu | Leu | Tyr | Leu 315 | Gln | Ala | Arg | Gly | Leu | Ala 320 | |
| Glu 305 | | | | | | | | | | | | | | | | |
| GTA | AAA | ACT | ATC | CAG | CAA | CAT | TTG | GGC | CAG | CTA | AAC | ATG | CTT | CAT | CGT | 1008 |
| Val | Lys | Thr | Ile | Gln 325 | Gln | His | Leu | Gly | Gln 330 | Leu | Asn | Met | Leu | His 335 | Arg | |
| CGG | TCC | GGG | CTG | CCA | CGA | CCA | AGT | GAC | AGC | AAT | GCT | GTT | TCA | CTG | GTT | 1056 |
| Arg | Ser | Gly | Leu 340 | Pro | Arg | Pro | Ser | Asp 345 | Ser | Asn | Ala | Val | Ser 350 | Leu | Val | |
| ATG | CGG | CGG | ATC | CGA | AAA | GAA | AAC | GTT | GAT | GCC | GGT | GAA | CGT | GCA | AAA | 1104 |
| Met | Arg | Arg 355 | Ile | Arg | Lys | Glu | Asn 360 | Val | Asp | Ala | Gly | Glu 365 | Arg | Ala | Lys | |
| CAG | GCT | CTA | GCG | TTC | GAA | CGC | ACT | GAT | TTC | GAC | CAG | GTT | CGT | TCA | CTC | 1152 |
| Gln | Ala 370 | Leu | Ala | Phe | Glu | Arg 375 | Thr | Asp | Phe | Asp | Gln 380 | Val | Arg | Ser | Leu | |
| ATG | GAA | AAT | AGC | GAT | CGC | TGC | CAG | GAT | ATA | CGT | AAT | CTG | GCA | TTT | CTG | 1200 |
| Met 385 | Glu | Asn | Ser | Asp | Arg 390 | Cys | Gln | Asp | Ile | Arg 395 | Asn | Leu | Ala | Phe | Leu 400 | |
| GGG | ATT | GCT | TAT | AAC | ACC | CTG | TTA | CGT | ATA | GCC | GAA | ATT | GCC | AGG | ATC | 1248 |
| Gly | Ile | Ala | Tyr | Asn 405 | Thr | Leu | Leu | Arg | Ile 410 | Ala | Glu | Ile | Ala | Arg 415 | Ile | |
| AGG | GTT | AAA | GAT | ATC | TCA | CGT | ACT | GAC | GGT | GGG | AGA | ATG | TTA | ATC | CAT | 1296 |
| Arg | Val | Lys | Asp 420 | Ile | Ser | Arg | Thr | Asp 425 | Gly | Gly | Arg | Met | Leu 430 | Ile | His | |

| | | | | | | | | | | | | | | | | |
|---|---|---|---|---|---|---|---|---|---|---|---|---|---|---|---|---|
| ATT | GGC | AGA | ACG | AAA | ACG | CTG | GTT | AGC | ACC | GCA | GGT | GTA | GAG | AAG | GCA | 1344 |
| Ile | Gly | Arg | Thr | Lys | Thr | Leu | Val | Ser | Thr | Ala | Gly | Val | Glu | Lys | Ala | |
| | | 435 | | | | 440 | | | | | | 445 | | | | |
| CTT | AGC | CTG | GGG | GTA | ACT | AAA | CTG | GTC | GAG | CGA | TGG | ATT | TCC | GTC | TCT | 1392 |
| Leu | Ser | Leu | Gly | Val | Thr | Lys | Leu | Val | Glu | Arg | Trp | Ile | Ser | Val | Ser | |
| 450 | | | | | 455 | | | | | | 460 | | | | | |
| GGT | GTA | GCT | GAT | GAT | CCG | AAT | AAC | TAC | CTG | TTT | TGC | CGG | GTC | AGA | AAA | 1440 |
| Gly | Val | Ala | Asp | Asp | Pro | Asn | Asn | Tyr | Leu | Phe | Cys | Arg | Val | Arg | Lys | |
| 465 | | | | | 470 | | | | | 475 | | | | | 480 | |
| AAT | GGT | GTT | GCC | GCG | CCA | TCT | GCC | ACC | AGC | CAG | CTA | TCA | ACT | CGC | GCC | 1488 |
| Asn | Gly | Val | Ala | Ala | Pro | Ser | Ala | Thr | Ser | Gln | Leu | Ser | Thr | Arg | Ala | |
| | | | | 485 | | | | | 490 | | | | | 495 | | |
| CTG | GAA | GGG | ATT | TTT | GAA | GCA | ACT | CAT | CGA | TTG | ATT | TAC | GGC | GCT | AAG | 1536 |
| Leu | Glu | Gly | Ile | Phe | Glu | Ala | Thr | His | Arg | Leu | Ile | Tyr | Gly | Ala | Lys | |
| | | | 500 | | | | | 505 | | | | | 510 | | | |
| GAT | GAC | TCT | GGT | CAG | AGA | TAC | CTG | GCC | TGG | TCT | GGA | CAC | AGT | GCC | CGT | 1584 |
| Asp | Asp | Ser | Gly | Gln | Arg | Tyr | Leu | Ala | Trp | Ser | Gly | His | Ser | Ala | Arg | |
| | | 515 | | | | 520 | | | | | | 525 | | | | |
| GTC | GGA | GCC | GCG | CGA | GAT | ATG | GCC | CGC | GCT | GGA | GTT | TCA | ATA | CCG | GAG | 1632 |
| Val | Gly | Ala | Ala | Arg | Asp | Met | Ala | Arg | Ala | Gly | Val | Ser | Ile | Pro | Glu | |
| | 530 | | | | | 535 | | | | | 540 | | | | | |
| ATC | ATG | CAA | GCT | GGT | GGC | TGG | ACC | AAT | GTA | AAT | ATT | GTC | ATG | AAC | TAT | 1680 |
| Ile | Met | Gln | Ala | Gly | Gly | Trp | Thr | Asn | Val | Asn | Ile | Val | Met | Asn | Tyr | |
| 545 | | | | | 550 | | | | | 555 | | | | | 560 | |
| ATC | CGT | AAC | CTG | GAT | AGT | GAA | ACA | GGG | GCA | ATG | GTG | CGC | CTG | CTG | GAA | 1728 |
| Ile | Arg | Asn | Leu | Asp | Ser | Glu | Thr | Gly | Ala | Met | Val | Arg | Leu | Leu | Glu | |
| | | | | 565 | | | | | 570 | | | | | 575 | | |
| GAT | GGC | GAT | TAG | | | | | | | | | | | | | 1740 |
| Asp | Gly | Asp | | | | | | | | | | | | | | |

( 2 ) INFORMATION FOR SEQ ID NO:11:

( i ) SEQUENCE CHARACTERISTICS:
( A ) LENGTH: 579 amino acids
( B ) TYPE: amino acid
( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met | Ser | Pro | Ile | Leu | Gly | Tyr | Trp | Lys | Ile | Lys | Gly | Leu | Val | Gln | Pro |
| 1 | | | | 5 | | | | | 10 | | | | | 15 | |
| Thr | Arg | Leu | Leu | Leu | Glu | Tyr | Leu | Glu | Glu | Lys | Tyr | Glu | Glu | His | Leu |
| | | | | 20 | | | | | 25 | | | | | 30 | |
| Tyr | Glu | Arg | Asp | Glu | Gly | Asp | Lys | Trp | Arg | Asn | Lys | Lys | Phe | Glu | Leu |
| | | | 35 | | | | | 40 | | | | | 45 | | |
| Gly | Leu | Glu | Phe | Pro | Asn | Leu | Pro | Tyr | Tyr | Ile | Asp | Gly | Asp | Val | Lys |
| | 50 | | | | | 55 | | | | | 60 | | | | |
| Leu | Thr | Gln | Ser | Met | Ala | Ile | Ile | Arg | Tyr | Ile | Ala | Asp | Lys | His | Asn |
| 65 | | | | | 70 | | | | | 75 | | | | | 80 |
| Met | Leu | Gly | Gly | Cys | Pro | Lys | Glu | Arg | Ala | Glu | Ile | Ser | Met | Leu | Glu |
| | | | | 85 | | | | | 90 | | | | | 95 | |
| Gly | Ala | Val | Leu | Asp | Ile | Arg | Tyr | Gly | Val | Ser | Arg | Ile | Ala | Tyr | Ser |
| | | | | 100 | | | | | 105 | | | | | 110 | |
| Lys | Asp | Phe | Glu | Thr | Leu | Lys | Val | Asp | Phe | Leu | Ser | Lys | Leu | Pro | Glu |
| | | | 115 | | | | | 120 | | | | | 125 | | |
| Met | Leu | Lys | Met | Phe | Glu | Asp | Arg | Leu | Cys | His | Lys | Thr | Tyr | Leu | Asn |
| | | 130 | | | | | 135 | | | | | 140 | | | |
| Gly | Asp | His | Val | Thr | His | Pro | Asp | Phe | Met | Leu | Tyr | Asp | Ala | Leu | Asp |
| 145 | | | | | 150 | | | | | 155 | | | | | 160 |

```
Val  Val  Leu  Tyr  Met  Asp  Pro  Met  Cys  Leu  Asp  Ala  Phe  Pro  Lys  Leu
               165            170                      175

Val  Cys  Phe  Lys  Lys  Arg  Ile  Glu  Ala  Ile  Pro  Gln  Ile  Asp  Lys  Tyr
          180                 185                      190

Leu  Lys  Ser  Ser  Lys  Tyr  Ile  Ala  Trp  Pro  Leu  Gln  Gly  Trp  Gln  Ala
          195                 200                 205

Thr  Phe  Gly  Gly  Gly  Asp  His  Pro  Pro  Lys  Ser  Asp  Leu  Val  Pro  Arg
     210                 215                      220

Gly  Ser  Arg  Arg  Ala  Ser  Val  Gly  Ser  His  Met  Pro  Met  Ala  Asn  Leu
225                      230                 235                           240

Leu  Thr  Val  His  Gln  Asn  Leu  Pro  Ala  Leu  Pro  Val  Asp  Ala  Thr  Ser
               245                      250                           255

Asp  Glu  Val  Arg  Lys  Asn  Leu  Met  Asp  Met  Phe  Arg  Asp  Arg  Gln  Ala
               260                 265                      270

Phe  Ser  Glu  His  Thr  Trp  Lys  Met  Leu  Leu  Ser  Val  Cys  Arg  Ser  Trp
          275                 280                      285

Ala  Ala  Trp  Cys  Lys  Leu  Asn  Asn  Arg  Lys  Trp  Phe  Pro  Ala  Glu  Pro
     290                 295                      300

Glu  Asp  Val  Arg  Asp  Tyr  Leu  Leu  Tyr  Leu  Gln  Ala  Arg  Gly  Leu  Ala
305                      310                 315                           320

Val  Lys  Thr  Ile  Gln  Gln  His  Leu  Gly  Gln  Leu  Asn  Met  Leu  His  Arg
               325                      330                           335

Arg  Ser  Gly  Leu  Pro  Arg  Pro  Ser  Asp  Ser  Asn  Ala  Val  Ser  Leu  Val
               340                      345                      350

Met  Arg  Arg  Ile  Arg  Lys  Glu  Asn  Val  Asp  Ala  Gly  Glu  Arg  Ala  Lys
          355                      360                      365

Gln  Ala  Leu  Ala  Phe  Glu  Arg  Thr  Asp  Phe  Asp  Gln  Val  Arg  Ser  Leu
     370                 375                      380

Met  Glu  Asn  Ser  Asp  Arg  Cys  Gln  Asp  Ile  Arg  Asn  Leu  Ala  Phe  Leu
385                      390                 395                           400

Gly  Ile  Ala  Tyr  Asn  Thr  Leu  Leu  Arg  Ile  Ala  Glu  Ile  Ala  Arg  Ile
               405                      410                           415

Arg  Val  Lys  Asp  Ile  Ser  Arg  Thr  Asp  Gly  Gly  Arg  Met  Leu  Ile  His
               420                      425                      430

Ile  Gly  Arg  Thr  Lys  Thr  Leu  Val  Ser  Thr  Ala  Gly  Val  Glu  Lys  Ala
          435                      440                      445

Leu  Ser  Leu  Gly  Val  Thr  Lys  Leu  Val  Glu  Arg  Trp  Ile  Ser  Val  Ser
     450                      455                      460

Gly  Val  Ala  Asp  Asp  Pro  Asn  Asn  Tyr  Leu  Phe  Cys  Arg  Val  Arg  Lys
465                      470                 475                           480

Asn  Gly  Val  Ala  Ala  Pro  Ser  Ala  Thr  Ser  Gln  Leu  Ser  Thr  Arg  Ala
               485                      490                           495

Leu  Glu  Gly  Ile  Phe  Glu  Ala  Thr  His  Arg  Leu  Ile  Tyr  Gly  Ala  Lys
               500                      505                      510

Asp  Asp  Ser  Gly  Gln  Arg  Tyr  Leu  Ala  Trp  Ser  Gly  His  Ser  Ala  Arg
          515                      520                 525

Val  Gly  Ala  Ala  Arg  Asp  Met  Ala  Arg  Ala  Gly  Val  Ser  Ile  Pro  Glu
     530                      535                 540

Ile  Met  Gln  Ala  Gly  Gly  Trp  Thr  Asn  Val  Asn  Ile  Val  Met  Asn  Tyr
545                      550                 555                           560

Ile  Arg  Asn  Leu  Asp  Ser  Glu  Thr  Gly  Ala  Met  Val  Arg  Leu  Leu  Glu
               565                      570                           575

Asp  Gly  Asp
```

( 2 ) INFORMATION FOR SEQ ID NO:12:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:12:

ATAACTTCGT ATAGCATACA TTATACGAAG TTAT     34

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:13:

ATTACCTCGT ATAGCATACA TTATACGAAG TTAT     34

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:14:

ATAACTTCGT ATAGCATACA TTATATGAAG TTAT     34

( 2 ) INFORMATION FOR SEQ ID NO:15:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:15:

ATTACCTCGT ATAGCATACA TTATATGAAG TTAT     34

( 2 ) INFORMATION FOR SEQ ID NO:16:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:16:

ATAACTTCGT ATAGTATACA TTATACGAAG TTAT     34

(2) INFORMATION FOR SEQ ID NO:17:

(i) SEQUENCE CHARACTERISTICS:
(A) LENGTH: 34 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "DNA"

(xi) SEQUENCE DESCRIPTION: SEQ ID NO:17:

ACAACTTCGT ATAATGTATG CTATACGAAG TTAT 34

(2) INFORMATION FOR SEQ ID NO:18:

(i) SEQUENCE CHARACTERISTICS:
(A) LENGTH: 34 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "DNA"

(xi) SEQUENCE DESCRIPTION: SEQ ID NO:18:

GAAGTTCCTA TTCTCTAGAA AGTATAGGAA CTTC 34